(12) United States Patent
Howard et al.

(10) Patent No.: US 11,464,930 B2
(45) Date of Patent: *Oct. 11, 2022

(54) SELF-ADJUSTING MASK SYSTEM

(71) Applicant: ResMed Pty Ltd, Bella Vista (AU)

(72) Inventors: Scott Alexander Howard, Sydney (AU); Karthikeyan Selvarajan, Sydney (AU); Christopher Scott Skipper, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/580,354

(22) Filed: Jan. 20, 2022

(65) Prior Publication Data

US 2022/0143347 A1 May 12, 2022

Related U.S. Application Data

(60) Continuation of application No. 15/814,811, filed on Nov. 16, 2017, which is a continuation of application No. 14/555,244, filed on Nov. 26, 2014, now Pat. No. 9,849,261, which is a division of application No. 12/379,940, filed on Mar. 4, 2009, now Pat. No. 8,950,403.

(Continued)

(51) Int. Cl.
*A61M 16/06* (2006.01)
*A61M 16/08* (2006.01)

(52) U.S. Cl.
CPC ........ *A61M 16/0622* (2014.02); *A61M 16/06* (2013.01); *A61M 16/065* (2014.02); *A61M 16/0611* (2014.02); *A61M 16/0616* (2014.02); *A61M 16/0633* (2014.02); *A61M 16/0638* (2014.02); *A61M 16/0644* (2014.02); *A61M 16/0683* (2013.01); *A61M 16/0825* (2014.02)

(58) Field of Classification Search
CPC .......... A61M 16/0605; A61M 16/0633; A61M 16/0644; A61M 16/065
See application file for complete search history.

(56) References Cited

U.S. PATENT DOCUMENTS

| 2,245,658 A | 6/1941 | Erickson |
| 5,074,297 A | 12/1991 | Venegas |

(Continued)

FOREIGN PATENT DOCUMENTS

| WO | WO 2006/074513 | 7/2006 |
| WO | WO 2006/074515 A1 | 7/2006 |

(Continued)

OTHER PUBLICATIONS

Two (2) Photos of Hsiner's CPAP/VPAP Face Mask Series (available at least by Oct. 2006).

(Continued)

*Primary Examiner* — Kathryn E Ditmer
(74) *Attorney, Agent, or Firm* — Nixon & Vanderhye P.C.

(57) ABSTRACT

A mask system including a frame module and a cushion module provided to the frame module and adapted to form a seal with the patient's face. The cushion module includes a main body defining a breathing chamber and adapted to interface with the frame module and a cushion adapted to form a seal with the patient's face. The main body and the cushion are comolded with one another.

19 Claims, 26 Drawing Sheets

Related U.S. Application Data

(60) Provisional application No. 61/136,488, filed on Sep. 9, 2008, provisional application No. 61/064,407, filed on Mar. 4, 2008.

(56) References Cited

U.S. PATENT DOCUMENTS

| | | |
|---|---|---|
| 5,662,101 A | 9/1997 | Ogden |
| 5,921,239 A | 7/1999 | McCall |
| 6,039,044 A | 3/2000 | Sullivan |
| 6,631,718 B1 | 10/2003 | Lovell |
| 6,732,733 B1 | 5/2004 | Brostrom |
| 7,000,614 B2 | 2/2006 | Lang et al. |
| 8,397,728 B2 | 3/2013 | D'Souza et al. |
| 8,490,623 B2 | 7/2013 | Berthon-Jones et al. |
| 8,517,023 B2 | 8/2013 | Henry |
| 8,550,084 B2 | 10/2013 | Ng et al. |
| 8,720,443 B2 | 5/2014 | Kooij et al. |
| 8,950,403 B2 | 2/2015 | Howard et al. |
| 9,381,316 B2 | 7/2016 | Ng et al. |
| 2002/0020416 A1 | 2/2002 | Namey |
| 2003/0075182 A1 | 4/2003 | Heidmann |
| 2004/0025881 A1 | 2/2004 | Gunaratnam |
| 2004/0065328 A1 | 4/2004 | Amarasinghe |
| 2004/0094157 A1 | 5/2004 | Dantanarayana |
| 2004/0144386 A1 | 7/2004 | Frater et al. |
| 2005/0005940 A1 | 1/2005 | Gunaratnam |
| 2006/0096598 A1 | 5/2006 | Ho |
| 2006/0118117 A1 | 6/2006 | Berthon/Jones |
| 2006/0124133 A1 | 6/2006 | Bierman |
| 2006/0201514 A1 | 9/2006 | Jones et al. |
| 2006/0272646 A1 | 12/2006 | Ho et al. |
| 2007/0044804 A1* | 3/2007 | Matula, Jr. ............ A61M 16/06 128/206.21 |
| 2008/0072909 A1 | 3/2008 | Sherman |
| 2008/0099023 A1* | 5/2008 | Berthon-Jones ............ A61M 16/0066 128/206.24 |
| 2008/0149105 A1 | 6/2008 | Matula |
| 2008/0178875 A1 | 7/2008 | Henry |
| 2008/0314388 A1 | 12/2008 | Brambilla |
| 2009/0223521 A1 | 9/2009 | Howard et al. |
| 2010/0163049 A1 | 7/2010 | Osier |
| 2015/0075533 A1 | 3/2015 | Howard et al. |
| 2018/0071475 A1 | 3/2018 | Howard et al. |

FOREIGN PATENT DOCUMENTS

| | | |
|---|---|---|
| WO | WO 2006/130903 | 12/2006 |
| WO | WO 2007/041751 A1 | 4/2007 |

OTHER PUBLICATIONS

Four (4) Photos of Hsiner's Comfo Mask Series (available at least by May 2008).

Pellethane™ material data sheet, accessed May 4, 2021 (Year: 2021), 1 page.

* cited by examiner

SELF-ADJUSTING MASK SYSTEM

CROSS-REFERENCE TO RELATED APPLICATIONS

This application is a continuation of U.S. application Ser. No. 15/814,811, filed Nov. 16, 2017, which is a continuation of U.S. application Ser. No. 14/555,244, filed Nov. 26, 2014, now U.S. Pat. No. 9,849,261, which is a divisional of U.S. application Ser. No. 12/379,940, filed Mar. 4, 2009, now U.S. Pat. No. 8,950,403, which claims the benefit of U.S. Provisional Application Nos. 61/064,407, filed Mar. 4, 2008, and 61/136,488, filed Sep. 9, 2008, each of which is incorporated herein by reference in its entirety.

FIELD OF THE INVENTION

The present invention relates to a mask system used for treatment, e.g., of Sleep Disordered Breathing (SDB) with Continuous Positive Airway Pressure (CPAP) or Non-Invasive Positive Pressure Ventilation (NIPPV).

BACKGROUND OF THE INVENTION

Patient interfaces, such as a full-face or nasal mask systems, for use with blowers and flow generators in the treatment of sleep disordered breathing (SDB), typically include a soft face-contacting portion, such as a cushion, and a rigid or semi-rigid shell or frame. In use, the interface is held in a sealing position by headgear so as to enable a supply of air at positive pressure (e.g., 2-30 cm H₂O) to be delivered to the patient's airways.

One factor in the efficacy of therapy and compliance of patients with therapy is the comfort and fit of the patient interface.

The present invention provides alternative arrangements of mask systems to enhance the efficacy of therapy and compliance of patients with therapy.

SUMMARY OF THE INVENTION

One aspect of the invention relates to a mask system including a frame module and a cushion module provided to the frame module and adapted to form a seal with the patient's face. The cushion module includes a main body defining a breathing chamber and adapted to interface with the frame module and a cushion adapted to form a seal with the patient's face. The main body and the cushion are comolded with one another.

Another aspect of the invention relates to a mask system including a cushion module including a main body defining a breathing chamber and a cushion adapted to form a seal with the patient's face, and an elbow module provided to the cushion module and adapted to be connected to an air delivery tube that delivers breathable gas to the patient. The main body and the cushion are comolded with one another.

Another aspect of the invention relates to a kit including a frame module, at least first and second cushion modules adapted to be provided to the frame module and adapted to form a seal with the patient's face, and an elbow module adapted to be provided to each of the at least first and second cushion modules and adapted to be connected to an air delivery tube that delivers breathable gas to the patient. The at least first and second cushion modules are different from one another in at least one aspect.

Another aspect of the invention relates to a method for constructing a mask system including molding a relatively hard part of a cushion module, co-molding a relatively soft part of the cushion module to the relatively hard part, and using an automated robot, grasping the relatively hard part and assembling the co-molded cushion module to another component of the mask system.

Another aspect of the invention relates to a method for fitting a mask system to a patient including providing a frame module, selecting a cushion based on a preferred cushion style, attaching a cushion module with the selected cushion to the frame module, selecting a vent style and/or impedance requirement, and attaching an elbow module with the selected vent style and/or impedance requirement to the cushion module.

Another aspect of the invention relates to a mask system including a frame module, a cushion module provided to the frame module and adapted to form a seal with the patient's face, an elbow module adapted to be connected to an air delivery tube that delivers breathable gas to the patient, and a dynamically adjustable connector provided between the frame module and the cushion module and/or between the elbow module and the frame module or the cushion module. Other locations of the dynamically adjustable connector are possible.

Another aspect of the invention relates to a mask system including a frame and a forehead support provided to a base of the frame by a movement region structured to allow adjustment of the frame relative to the forehead support.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1-2 is a front view of the mask system shown in FIG. 1-1;

FIG. 1-3 is a side view of the mask system shown in FIG. 1-1;

FIG. 1-4 is a bottom view of the mask system shown in FIG. 1-1;

FIG. 2 is an exploded view of the mask system shown in FIG. 1-1;

FIG. 3-1 is a rear perspective view of a frame module of the mask system shown in FIG. 1-1;

FIG. 3-2 is a side view of the frame module shown in FIG. 3-1;

FIG. 4-1 is a front perspective view of a cushion module of the mask system shown in FIG. 1-1;

FIG. 4-2 is a rear perspective view of the cushion module shown in FIG. 4-1;

FIG. 4-3 is a side view of the cushion module shown in FIG. 4-1;

FIG. 4-4 is an exemplary cross-sectional view through the cushion module according to an embodiment of the present invention;

FIG. 4-5 is a schematic view illustrating the cushion module pivotally mounted to the frame module according to an embodiment of the present invention;

FIG. 4-6 is a schematic view illustrating a locking arrangement for coupling the cushion module to the frame module according to an embodiment of the present invention;

FIG. 4-7 is a side view of a mask system including a flexible member according to an embodiment of the present invention;

FIG. 4-8 is a side view of a mask system including a flexible member according to another embodiment of the present invention;

FIG. 4-9 is a perspective view of a mask system including flexible members according to another embodiment of the present invention;

FIG. 4-10 is an exploded view of the mask system shown in FIG. 4-9;

FIG. 4-11 is a perspective view of a mask system including flexible members according to another embodiment of the present invention;

FIG. 4-12 is a perspective view of a mask system including a continuous flexible member according to another embodiment of the present invention;

FIG. 4-13 is a front view of a frame and forehead support according to an embodiment of the present invention;

FIG. 4-14 is a partial perspective view of the forehead support of FIG. 4-13;

FIG. 4-15 is a side view showing coarse adjustment of the frame and forehead support of FIG. 4-13;

FIG. 4-16 is a side view showing fine adjustment of the frame and forehead support of FIG. 4-13;

FIG. 4-17 is a side view showing a co-molded base of the forehead support of FIG. 4-13 according to an embodiment of the present invention;

FIG. 4-18 is a cross-sectional view showing the base of a forehead support detachably connected to a frame according to an embodiment of the present invention;

FIG. 5-1 is a front perspective view of an elbow module of the mask system shown in FIG. 1-1;

FIG. 5-2 is a rear perspective view of the elbow module shown in FIG. 5-1;

FIG. 5-3 is a side view of the elbow module shown in FIG. 5-1;

FIG. 6 is a front perspective view of the mask system shown in FIG. 1-1 with the elbow module arranged in a different orientation;

FIG. 7 is a schematic view of a cushion module, elbow module, and vent module according to another embodiment of the present invention;

FIGS. 8-1 and 8-2 are cross-sectional views showing an elbow module attachment according to an embodiment of the present invention; and FIG. 9 is a cross-sectional view showing an elbow module attachment according to another embodiment of the present invention.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

While each embodiment below is described as including a nasal interface type, each embodiment may be adapted for use with other suitable interface types. That is, the interface type is merely exemplary, and each embodiment may be adapted to include other interface types, e.g., full face interface, etc.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. Mask System

FIGS. 1-1 to 1-4 and 2 illustrate a mask system 10 according to an embodiment of the present invention. In this embodiment, the mask system 10 includes a nasal interface. The mask system 10 includes a frame module 20, a cushion module 40 provided to the frame module 20 and adapted to form a seal with the patient's face, and an elbow module 70 provided to the cushion module 40 and adapted to be connected to an air delivery tube (not shown) that delivers breathable gas to the patient. Headgear may be removably attached to the frame module 20 to maintain the mask system 10 in a desired adjusted position on the patient's face. The mask system 10 is intended for use in positive pressure therapy for users with obstructive sleep apnea (OSA) or another respiratory disorder.

As described below, the mask system 10 provides a modular design that allows different styles and/or sizes of the frame module 20, cushion module 40, and elbow module 70 to be interchanged or mixed and matched with one another to provide a more customized mask system for the patient. In addition, such design allows selected modules to be easily replaced, e.g., treatment requirements change, worn out or damaged, etc.

1.1 Frame Module

The frame module 20 is structured to maintain the cushion module 40 in an operative position with respect to the patient's face. In addition, the frame module 20 is structured to removably attach to headgear adapted to maintain the mask system 10 in a desired position on the patient's face.

Figure 1:
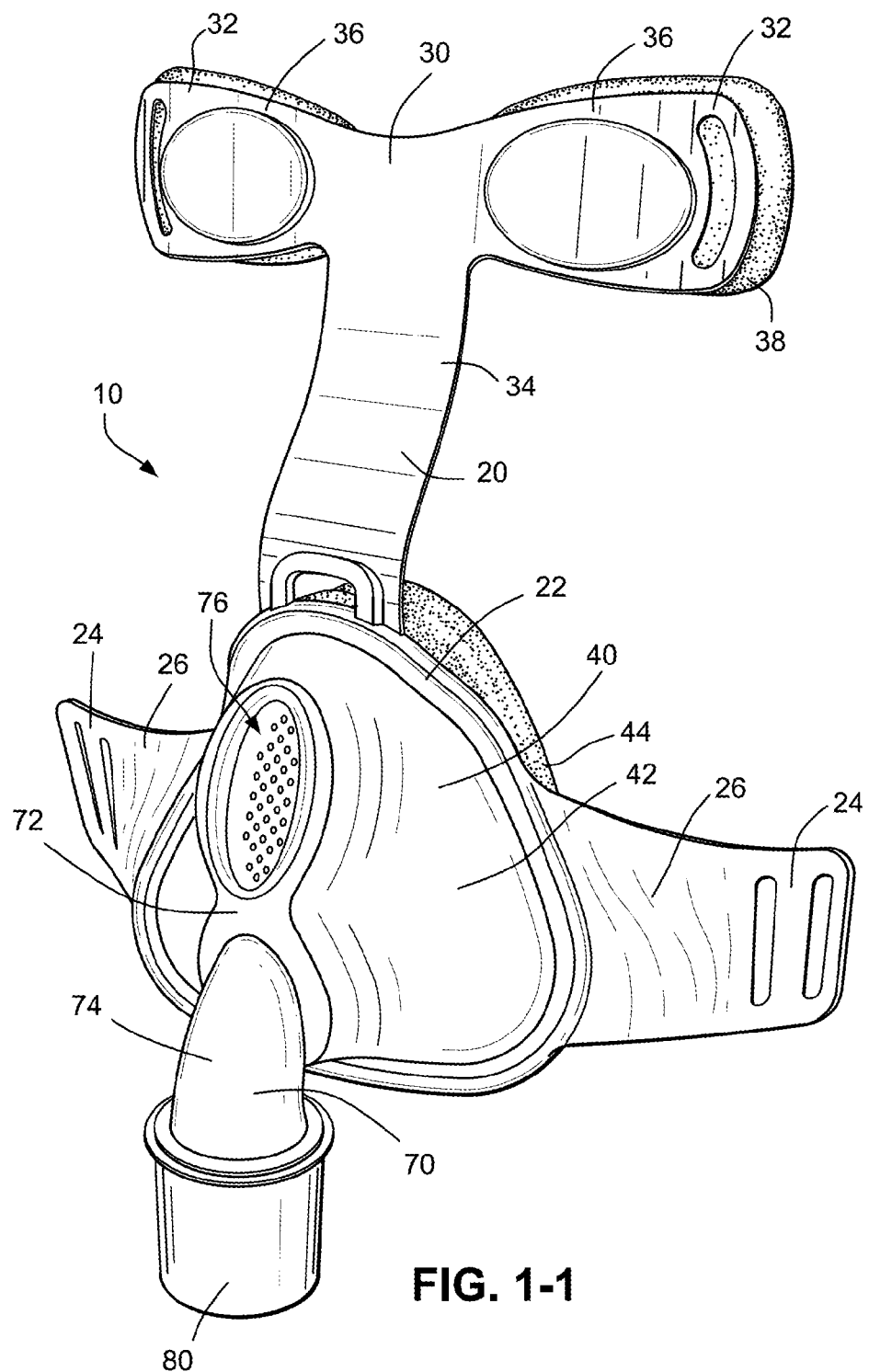
FIG. 1-1 is a front perspective view of a mask system according to an embodiment of the present invention.
Figures 1, 2:
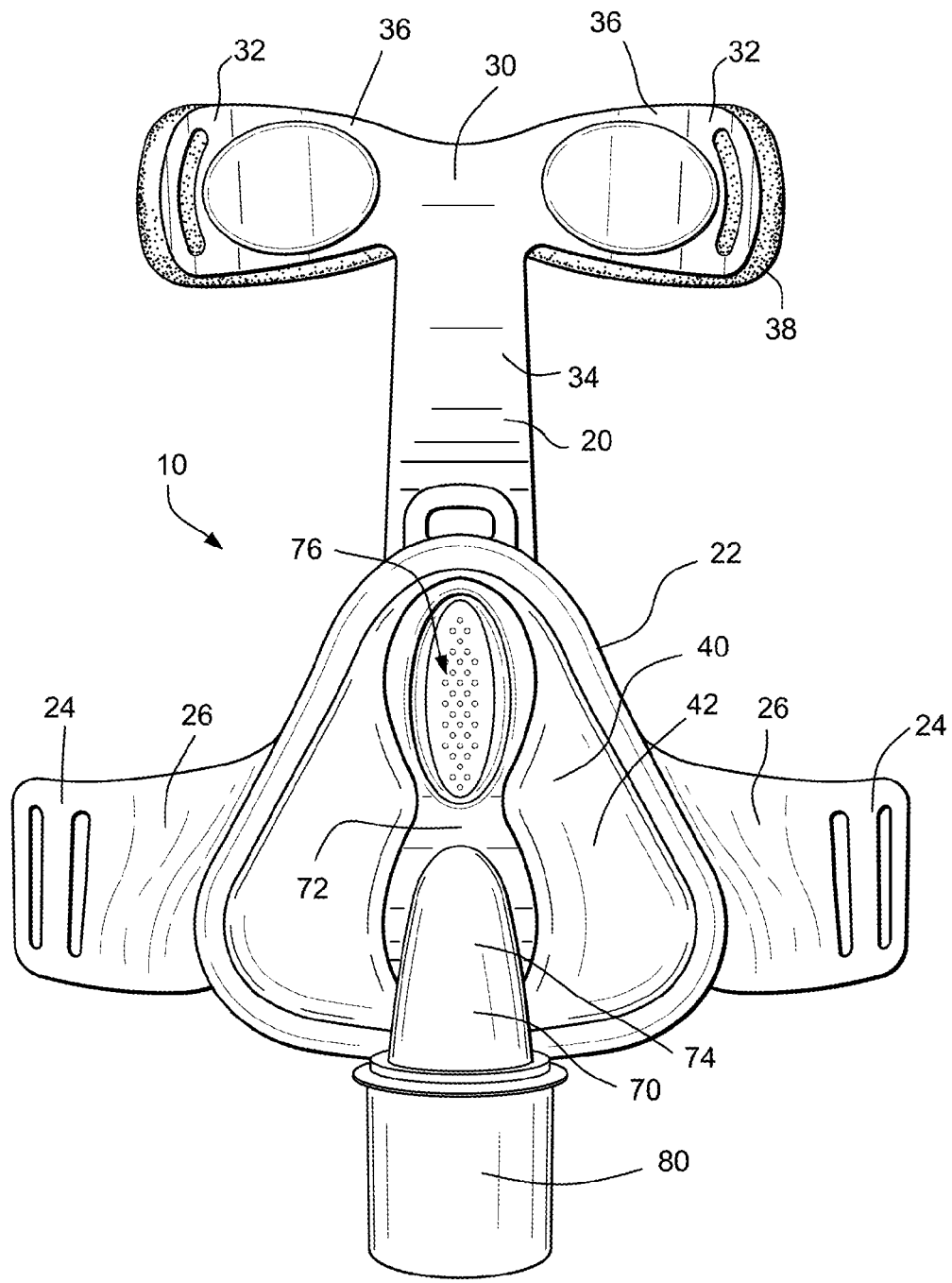
Figures 1, 2, 3:
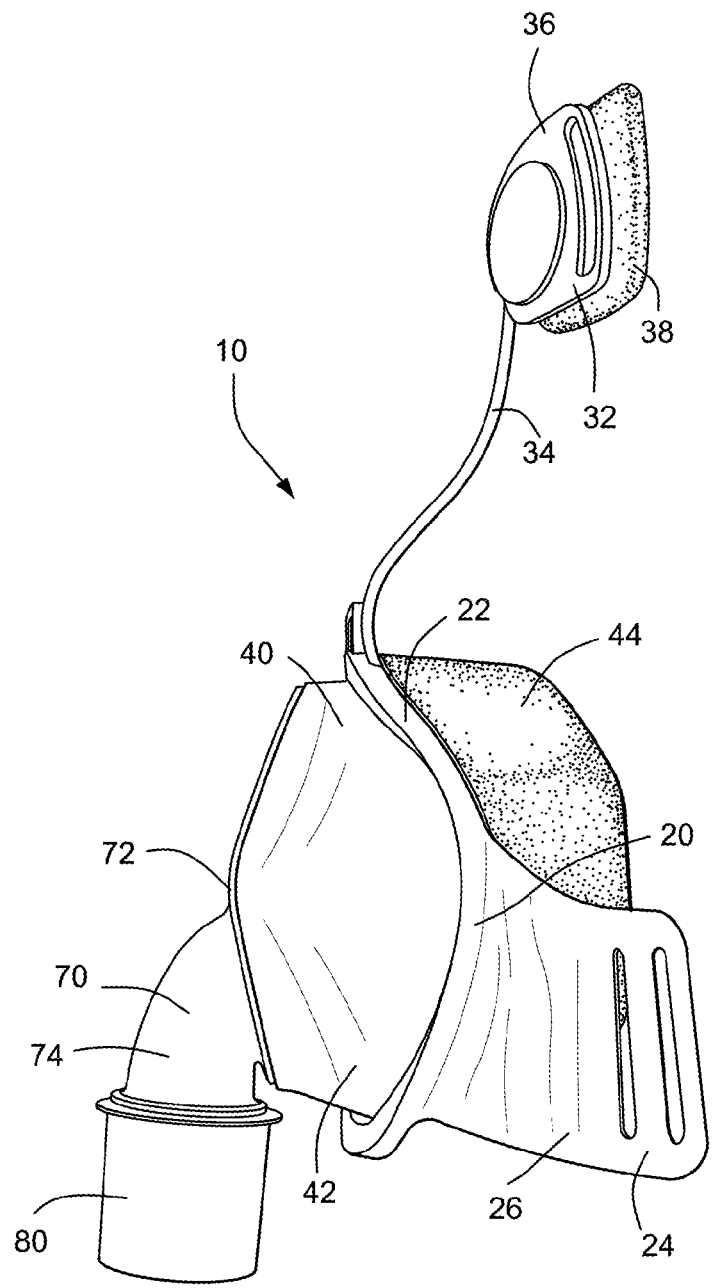

As best shown in FIGS. 2 and 3-1 to 3-2, the frame module 20 includes an open construction that provides an annular cushion retaining portion 22 structured to retain the cushion module 40. The frame module 20 may also include one or more additional components, such as a fixed forehead support 30 that extends from a top of the cushion retaining portion 22, and/or headgear connectors 24 provided to respective sides of the cushion retaining portion 22. Headgear connectors 32 may be provided to respective sides of the forehead support 30. Each headgear connector 24, 32 has at least one slot adapted to receive a respective headgear strap in use.

The frame module 20 may be constructed from a wide range of materials (e.g., polycarbonate, polypropylene, thermoplastic elastomer (TPE), Pocan®, etc.) and may include styling options for comfort and/or aesthetics. For example, the frame module 20 may be constructed of TPE, which provides a relatively soft structure, coloring options, flexibility, and gripping options. In another embodiment, TPE may be overmolded to one or more portions of the frame module 20, e.g., along forehead support, etc. In another embodiment, the frame module 20 may include flocking to provide softness, coloring, textured gripping, etc. Also, an in-mold design may be provided to the frame module 20, e.g., logo and/or aesthetic features integrally molded with the frame module.

In the illustrated embodiment, each headgear connector 24 includes an arm 26 that is suitably contoured so as to engage a respective cheek of the patient in use. As indicated in dashed lines in FIG. 3-1, a cheek pad 28 (e.g., constructed of TPE) may be provided to the inner surface of the arm 26 to support the arm 26 on the patient's cheek and stop bottoming out of the frame module 20 on the patient's face in use.

1.1.1 Forehead Support

The forehead support 30 provides a support and stability mechanism between the mask system 10 and the patient's forehead. The forehead support 30 has a general "T"-shape, with a base 34 and a pair of arms 36 arranged along the upper cross portion of the "T". Each arm 36 supports an elastomeric or foam forehead pad 38 that is structured to engage a patient's forehead in use. In addition, each end of the arm 36 provides a headgear connector 32 (e.g., slot) adapted to receive a respective headgear strap.

In the illustrated embodiment, the forehead support 30 has a substantially fixed setting. However, as shown in FIG. 3-2, the base 34 of the forehead support 30 is contoured along its length and may include some inherent flexibility to allow a range of adjustment. Also, adjustment may be provided by adjusting the position of the cushion module 40 with respect to the frame module 20 as described in greater detail below. However, the forehead support 30 may be structured to include some form of mechanical adjustment.

In an alternative embodiment, the frame module 20 may not include a forehead support, and additional headgear connectors may be provided to the cushion retaining portion 22 to receive respective headgear straps, e.g., upper and lower headgear connectors on each side of the cushion retaining portion.

1.1.2 Headgear Attachment

Headgear may be removably attached to the headgear connectors 32 of the forehead support 30 and the headgear connectors 24 of the cushion retaining portion 22 to maintain the mask system 10 in a desired position on the patient's face.

For example, the headgear may include a pair of upper and lower straps with the upper straps removably connected to headgear connectors 32 provided on the forehead support 30 and the lower straps removably connected to headgear connectors 24 provided on the cushion retaining portion 22. However, headgear straps may be secured to the frame module 20 in other suitable manners, e.g., clip arrangement, adjustable ladder-lock arrangement, etc.

In an embodiment, the headgear may include a similar headgear arrangement as that disclosed in PCT application no. PCT/AU2006/000770, filed Jun. 6, 2006, which is incorporated herein by reference in its entirety.

In an alternative embodiment, the headgear may be molded (e.g., from TPE). In such arrangement, forehead pads may be incorporated into the molded upper straps of the headgear.

1.1.3 Frame Module Profile

As illustrated, the frame module 20 has a low profile when viewed from the side (e.g., see FIGS. 1-3 and 3-2). That is, the frame module 20 is contoured so that it closely follows the contours of the patient's face. In use, the frame module 20 is substantially flush with the patient's face and does not substantially protrude from the patient's face. As a result, the frame module 20 is less obtrusive and does not significantly affect the patient's field of view.

1.2 Cushion Module

The cushion module 40 is structured to interface with the frame module 20 and form a seal with patient's nose in use. In addition, the cushion module 40 is structured to maintain the elbow module 70 in an operative position.

As best shown in FIGS. 2 and 4-1 to 4-3, the cushion module 40 includes a main body 42 and a cushion 44 provided to the main body 42. The main body 42 is constructed of a relatively rigid material (e.g., polycarbonate) and the cushion 44 is constructed of a relatively soft elastomeric material (e.g., silicone or foam). In use, the main body 42 defines a breathing chamber and is adapted to interface with or otherwise attach to the frame module 20 and the cushion 44 is adapted to form a seal with the patient's nose. Also, the main body 42 includes an opening 46 that is adapted to interface with or otherwise attach to the elbow module 70.

Figures 1, 2, 3, 4:
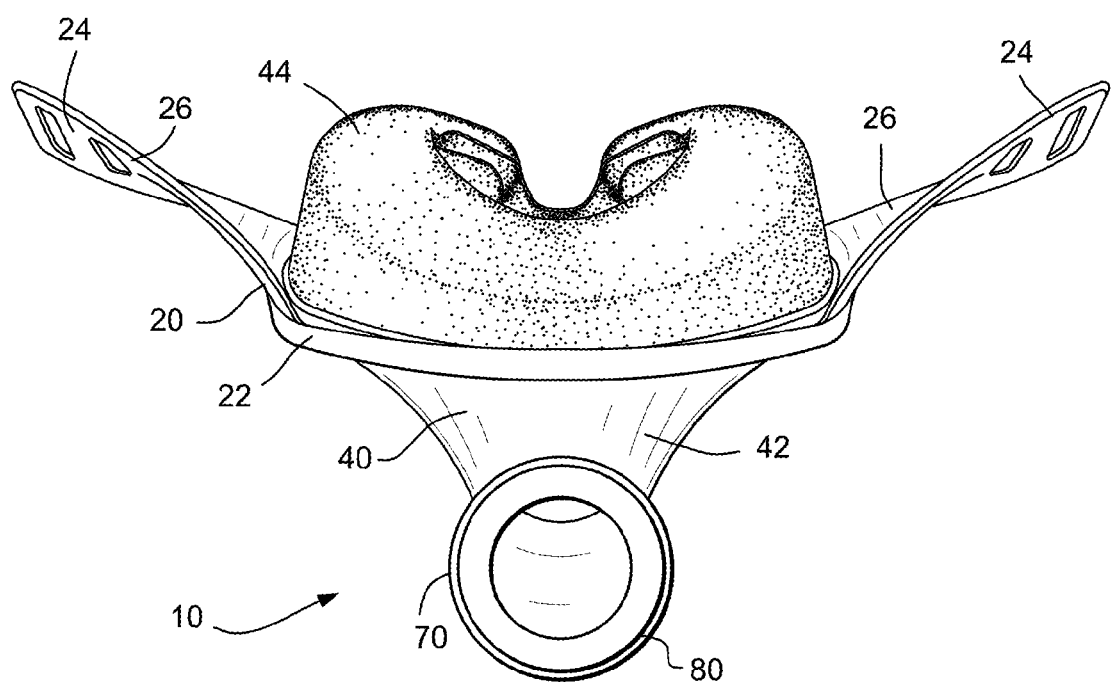
Figure 2:
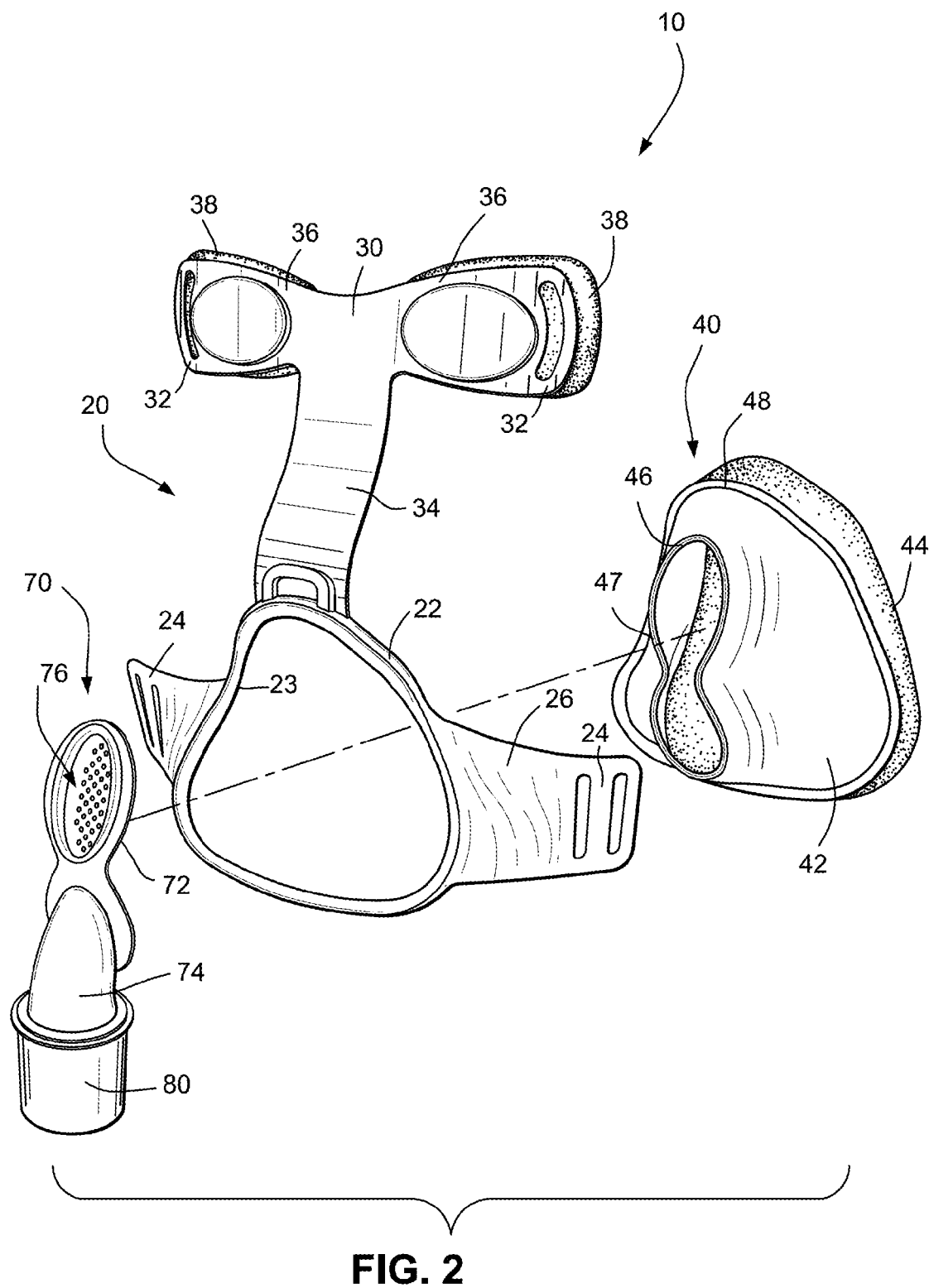
Figures 1, 3:
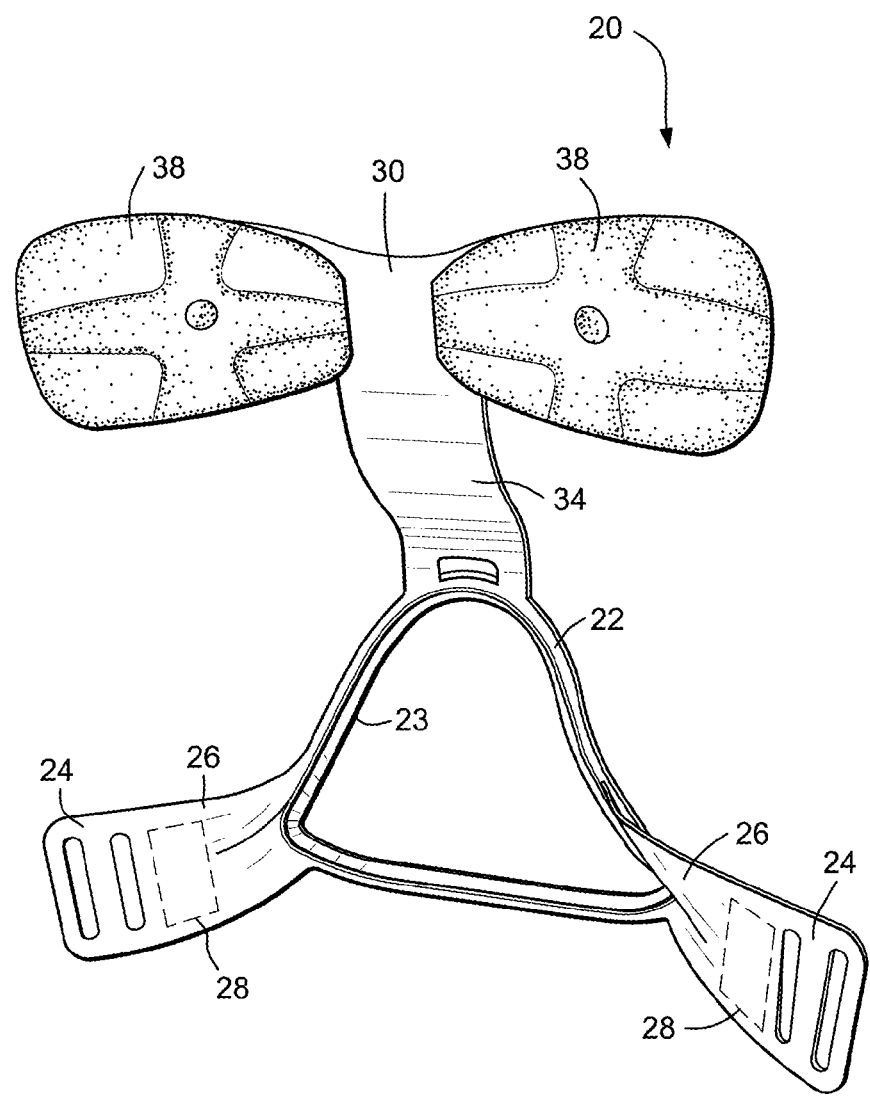
Figures 2, 3:
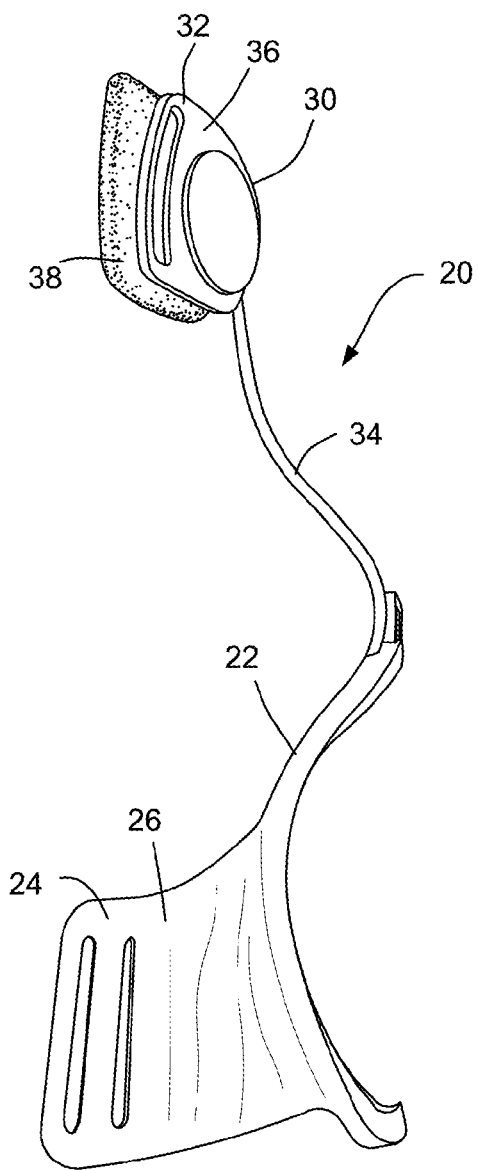

In the illustrated embodiment, the cushion 44 is a nasal cushion adapted to engage the patient's face generally along nasal bridge, cheek, and upper lip regions of the patient's face. As shown in FIG. 4-2, the cushion 44 includes a base wall 44(1) provided to the main body 42, an undercushion layer (UCL) 44(2) extending away from the base wall 44(1), and a membrane 44(3) provided to substantially cover the UCL 44(2) and provide a sealing structure. In an embodiment, the cushion 44 may include a cushion structure similar to that disclosed in PCT application no. PCT/AU2006/000032, filed Jan. 12, 2006, which is incorporated herein by reference in its entirety. However, other cushion interfaces and structures are possible, e.g., full-face.

Also, the mask system 10 may be provided with a number of different cushion modules 40, e.g., each having cushions of different styles and/or sizes (e.g., depending on patient preference and/or fit). For example, the main body 42 of each cushion module may include a common or universal configuration for use with the frame module 20, and the cushion 44 may include different styles and/or sizes. This provides a modular arrangement that allows the frame module 20 to be selectively and removably coupled to one of multiple cushion modules. For example, the different cushion modules may include different size cushions (e.g., small, medium, and large) and may include a different cushion structures.

Similarly, the cushion module 40 may be provided with different frame modules 20, e.g., each frame module having a different style and/or size (e.g., frame module without forehead support, frame module with different arrangement/ style of headgear connectors, etc).

1.2.1 Co-Molding

In the illustrated embodiment, the main body 42 and cushion 44 are co-molded with one another to form a one-piece, integrated component. For example, the main body 42 may be molded of a relatively rigid material (e.g., polycarbonate) and the cushion 44 may be co-molded onto the main body 42 of a relatively soft elastomeric material (e.g., silicone).

In an embodiment, the main body 42 may be molded from a high temperature, biocompatible polycarbonate structured to maintain its structure (e.g., Bayer Apec 1745 polycarbonate). The cushion 44 may be comolded to the main body 42 from a silicone material that is able to chemically bond or self-adhere to the polycarbonate material of the main body 42 (e.g., Shinetsu KE-2090-40 Duro silicone). In an embodiment, the silicone cushion 44 may have a uniform thickness to reduce material usage and provide faster cycle times. However, other suitable materials are possible.

The outer perimeter of the main body 42 provides an interfacing structure 48 (e.g., land area) structured to bond with the base wall 44(1) of the cushion 44. In an embodiment, the interfacing structure 48 may provide the minimum land area to achieve an adequate bond with the cushion 44. Such bond may be made stronger by increasing the land area.

In an embodiment, flow bias of the mold material may be utilized when forming the cushion module 40. For example, FIG. 4-4 is an exemplary cross-sectional view illustrating the cushion 44 co-molded to the main body 42. As illustrated, the interfacing structure 48 may include a projection 48(1) structured to provide sufficient land area to bond with the cushion base wall 44(1). As material first flows into the path of least resistance during molding, an inner portion 44(1)-1 of the cushion base wall 44(1) may be designed to be thicker than an outer portion 44(1)-2 of the cushion base wall 44(1) (e.g., 20-40% thicker) so material flows first into the mold for the inner portion 44(1)-1 before it flows into the mold for the outer portion 44(1)-2. This arrangement forces air in the direction of the outer portion 44(1)-2 to ensure a complete part with no air trapped in the mold for the inner portion 44(1)-1.

Co-molding the main body 42 to the cushion 44 provides a chemical bond without a mechanical interlock. As a result, the connection includes no cracks, a gas tight seal, and clean interface. Moreover, such co-molded connection relaxes tolerances as the mold materials are sufficiently flexible to fill in any gaps at the interface between the main body 42 and the cushion 44.

1.2.2 Automated Manufacturing

The co-molded cushion module 40 also facilitates automated manufacturing. That is, the co-molded cushion module 40 includes a relatively hard part (i.e., the main body 42) and a relatively soft part (i.e., the cushion 44), and the relatively hard part is easier to handle and manipulate during assembly. For example, an automated robot may grasp the hard part of the cushion module 40 to manipulate the same for assembly to the frame module 20. Typically, cushion components are difficult to grasp with an automated robot (e.g., due to its relative softness) and require manual assembly to a relatively rigid frame. The cushion module 40 allows the entire mask system to be robotically assembled as each component of the mask system (i.e., frame module 20, cushion module 40, elbow module 70) includes a relatively hard part that can be gripped by an automated robot. In an alternative embodiment, each mask component may include other suitable structure to facilitate gripping by an automated robot, e.g., a relatively thick silicone portion that could be gripped by a robot.

In an embodiment, a method for making and assembling the mask system 10 may include molding the relatively hard part (i.e., the main body 42) of the cushion module 40, inserting the hard part into a silicone mold by a robot, injecting or otherwise molding the relatively soft part (i.e., the silicone cushion 44) to the relatively hard part, removing the co-molded cushion module 40 from the mold by a robot, and assembling the cushion module 40 to the remaining components of the mask system 10, i.e., all of which have a relatively hard part that can be gripped by a robot.

1.2.3 Cushion Module Attachment to Frame Module

The frame module 20 is structured to maintain the cushion module 40 in an operative position with respect to the patient's face.

In the illustrated embodiment, the annular cushion retaining portion 22 includes a flange or interfacing structure 23 (e.g., see FIG. 3-1) along its peripheral edge that is adapted to interface with or otherwise removably connect to the interfacing structure 48 along the outer perimeter of the main body 42 of the cushion module 40. The interfacing structures 23, 48 may connect with a friction fit, snap-fit, mechanical interlock, or other suitable attachment mechanism. However, other suitable arrangements for attaching the cushion module 40 to the frame module 20 are possible.

For example, the cushion module 40 may be coupled to the frame module 20 in a manner that allows the cushion module 40 to be locked in different angular positions with respect to the frame module 40. This arrangement allows the cushion module 40 to be selectively angled to enhance seal, comfort, adjust positioning of forehead support, etc.

Figures 1, 4:
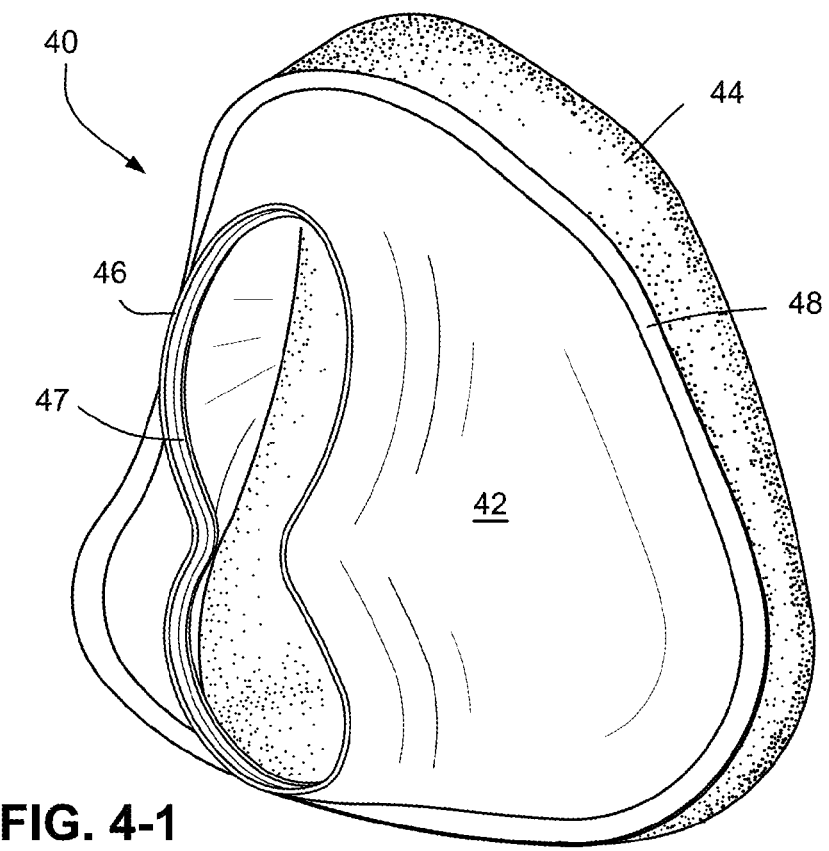
Figures 2, 4:
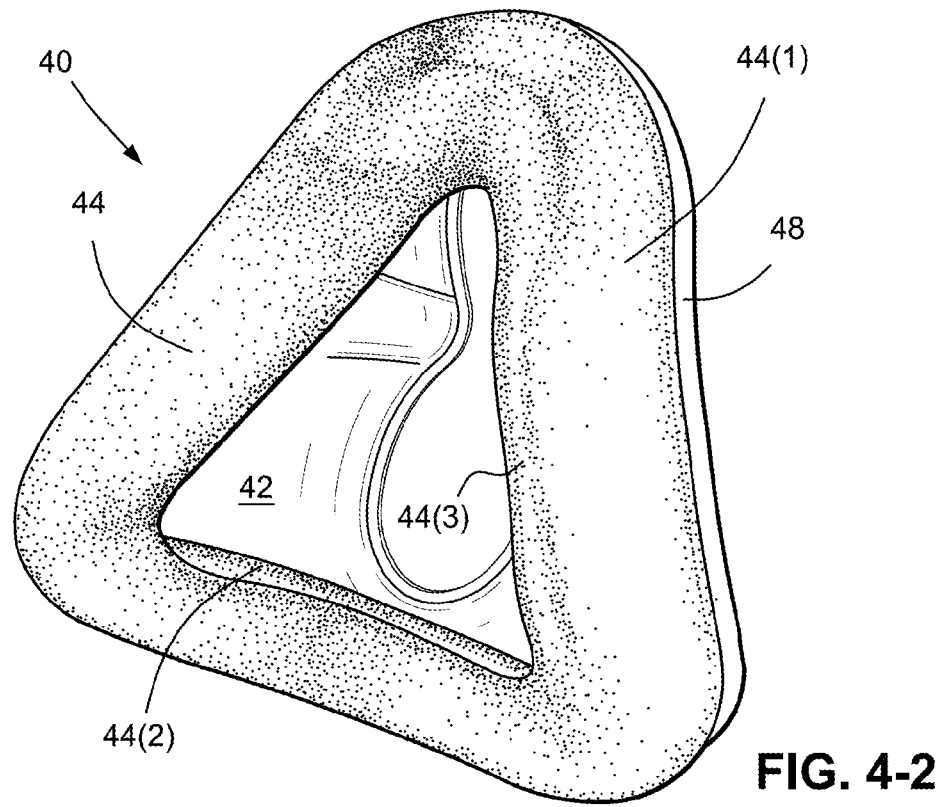
Figures 3, 4:
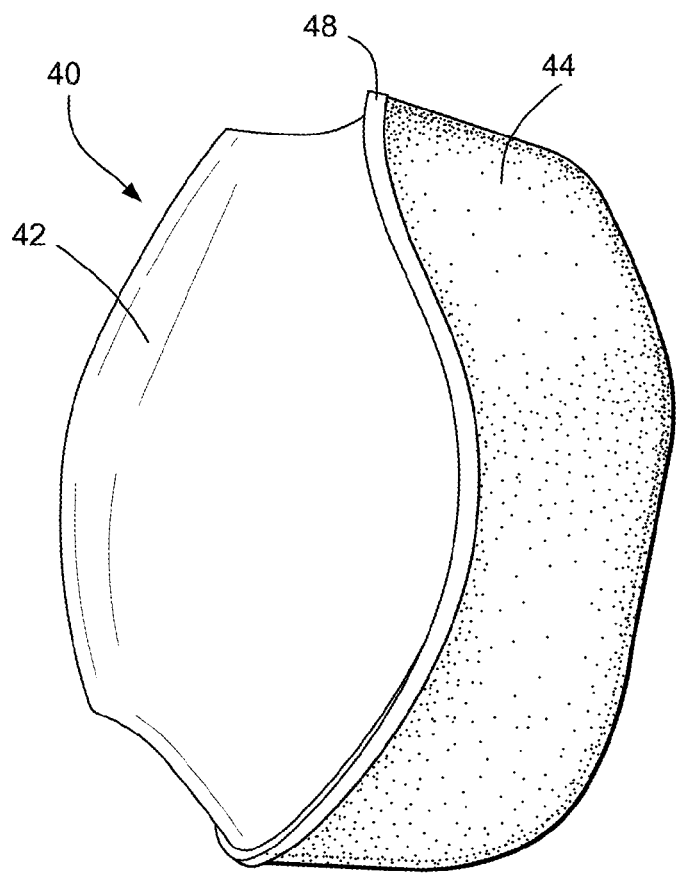
Figure 4:
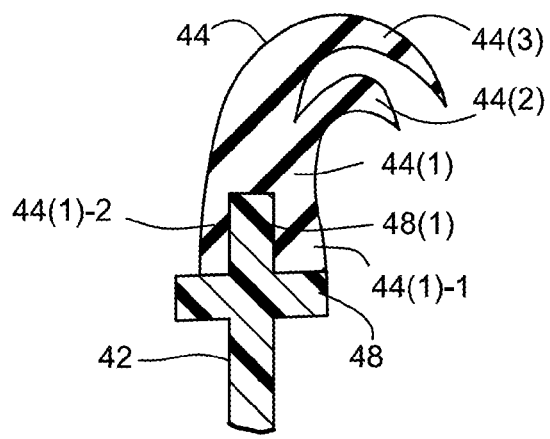
Figures 4, 5:
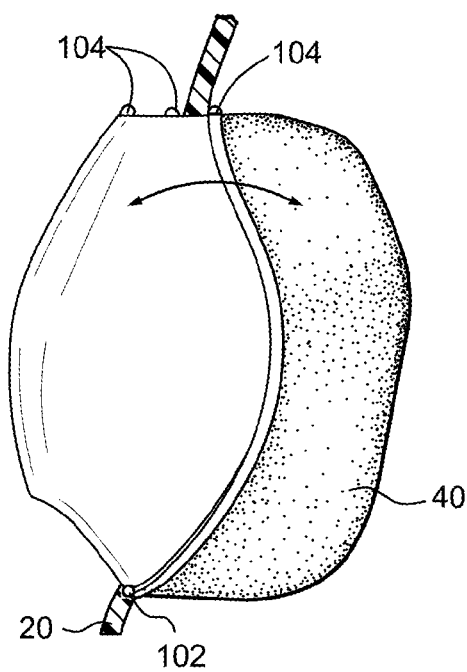

For example, as shown in FIG. 4-5, the cushion module 40 may be pivotally mounted to the frame module 20 (e.g., via pivot 102), and the cushion module 40 may include one or more locking lugs or a ratchet/gear arrangement 104 to lock the cushion module 40 to the frame module 20 in different angular positions. It should be appreciated that the location of the pivot/lugs may be reversed, and that the pivoting/locking arrangement may include other suitable structures.

Figures 4, 5, 6:
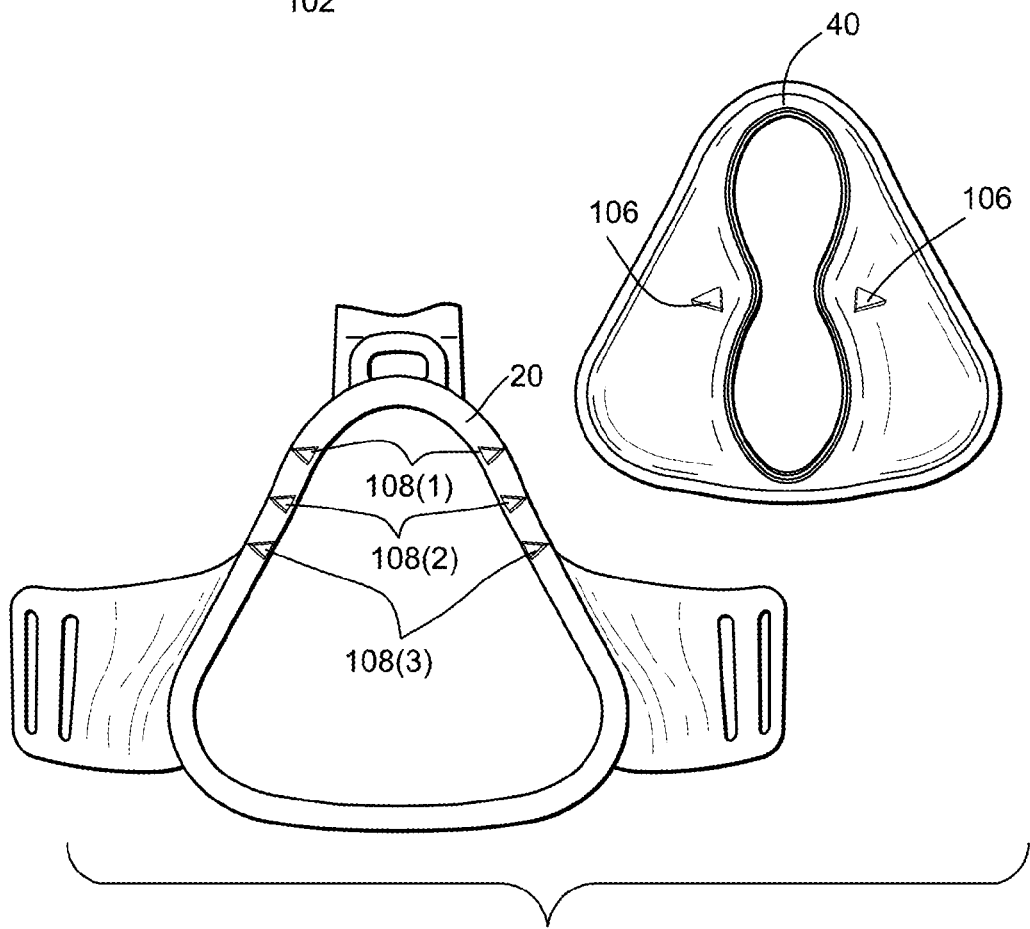

In an alternative embodiment, as shown in FIG. 4-6, the cushion module 40 may include protrusions 106 that are adapted to interlock with selected recesses 108(1), 108(2), 108(3) provided to the frame module 20 (i.e., recesses oriented at different heights, angles, etc.) to change the positioning or angle of the cushion module 40 with respect to the frame module 20. It should be appreciated that the number and placement of the protrusions/recesses may be changed.

In another alternative embodiment, a biasing arrangement may be provided between the frame module 20 and cushion module 40 to provide a biasing force between the frame module 20 and the cushion module 40. Such biasing force may bias the cushion module 40 into the patient's face in use, e.g., to enhance seal.

In another embodiment, the mask system may be self-fitting so that the cushion module 40 is structured to self adjust as it is positioned into engagement with the patient's face. Such self-fitting mask system may also be manually adjustable and/or lockable by the patient.

FIGS. 4-7 to 4-11 illustrate alternative embodiments of a self-fitting mask system in which one or more flexible members join the cushion module to the frame module. In use, the one or more flexible members are structured to allow adjustment of the cushion module with respect to the frame module, i.e., flexible members add flexibility and articulation of the cushion module with respect to the frame module. That is, the cushion module can selectively adjust and/or self-fit to the patient's face against biasing from the one or more flexible members.

Figures 4, 5, 6, 7:
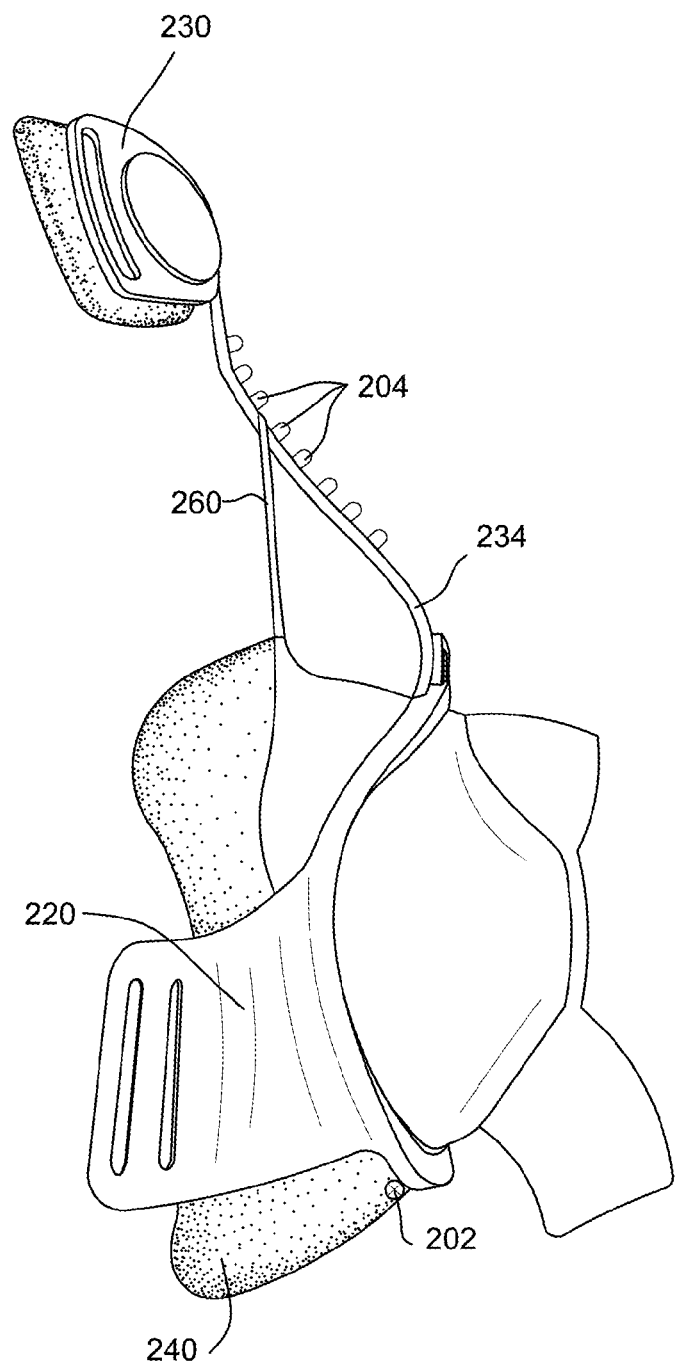
Figures 4, 5, 6, 7, 8:
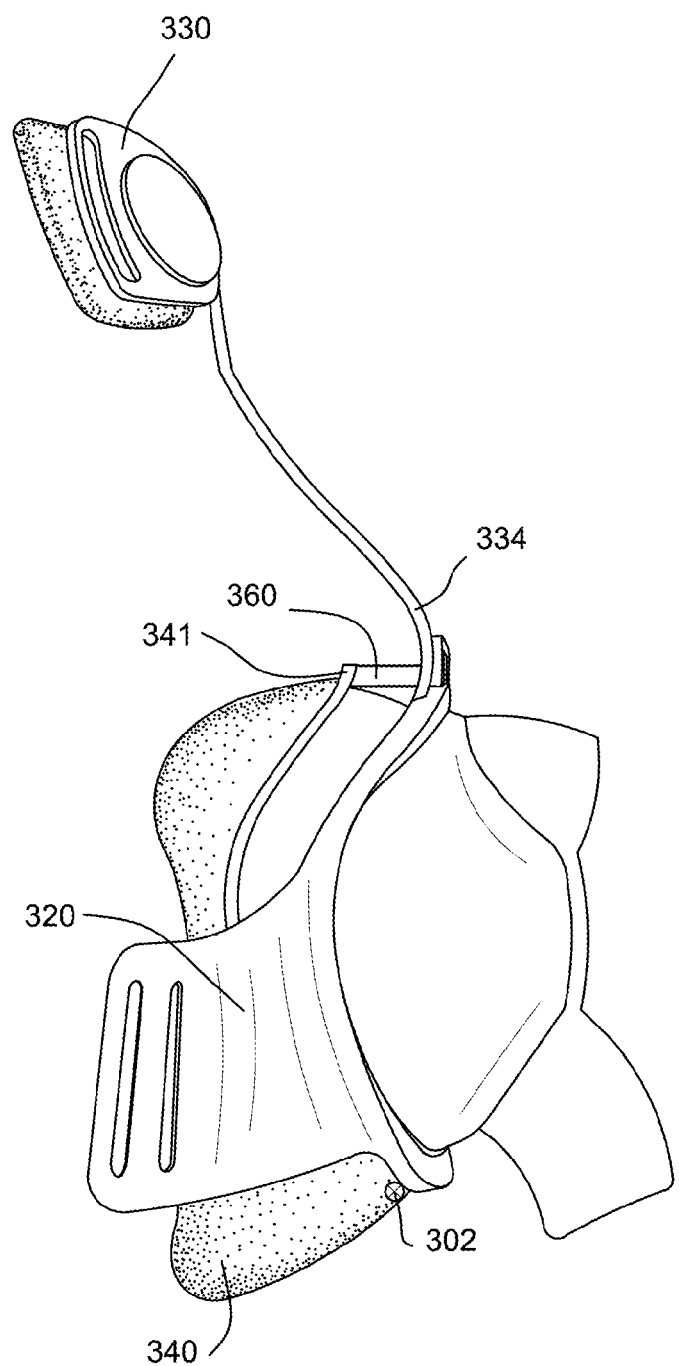
Figures 4, 5, 6, 7, 8, 9:
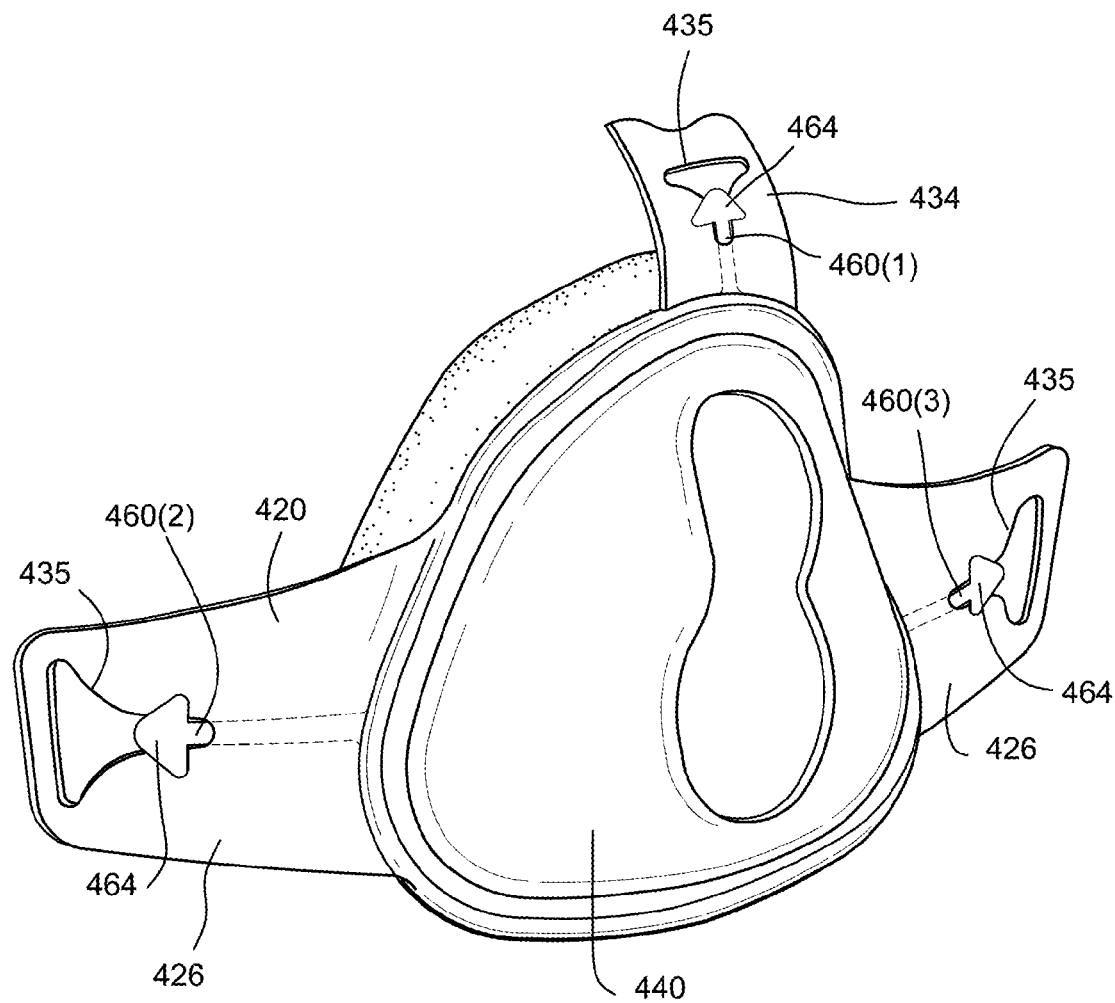
Figures 4, 5, 6, 7, 8, 9, 10:
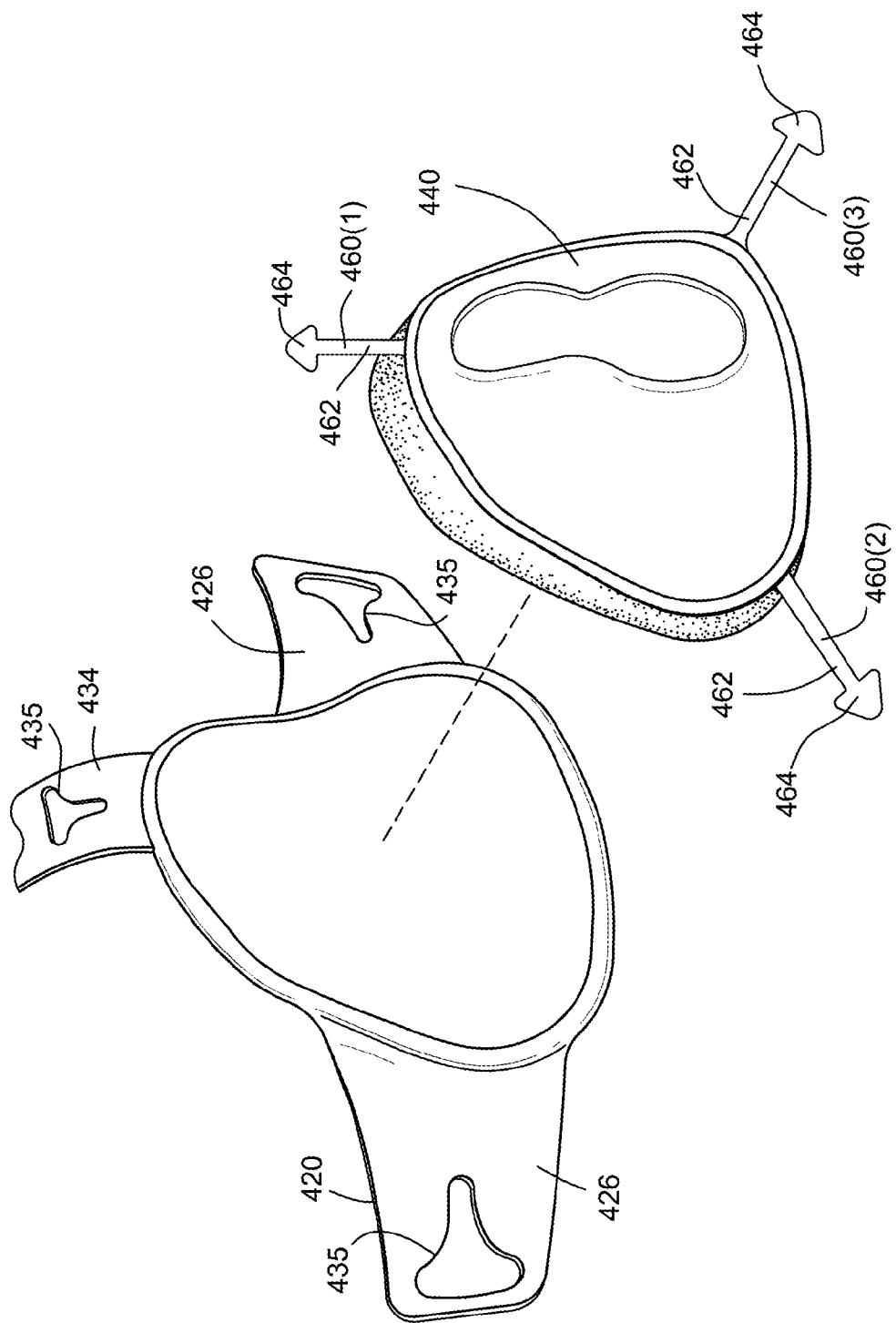
Figures 4, 5, 6, 7, 8, 9, 10, 11:
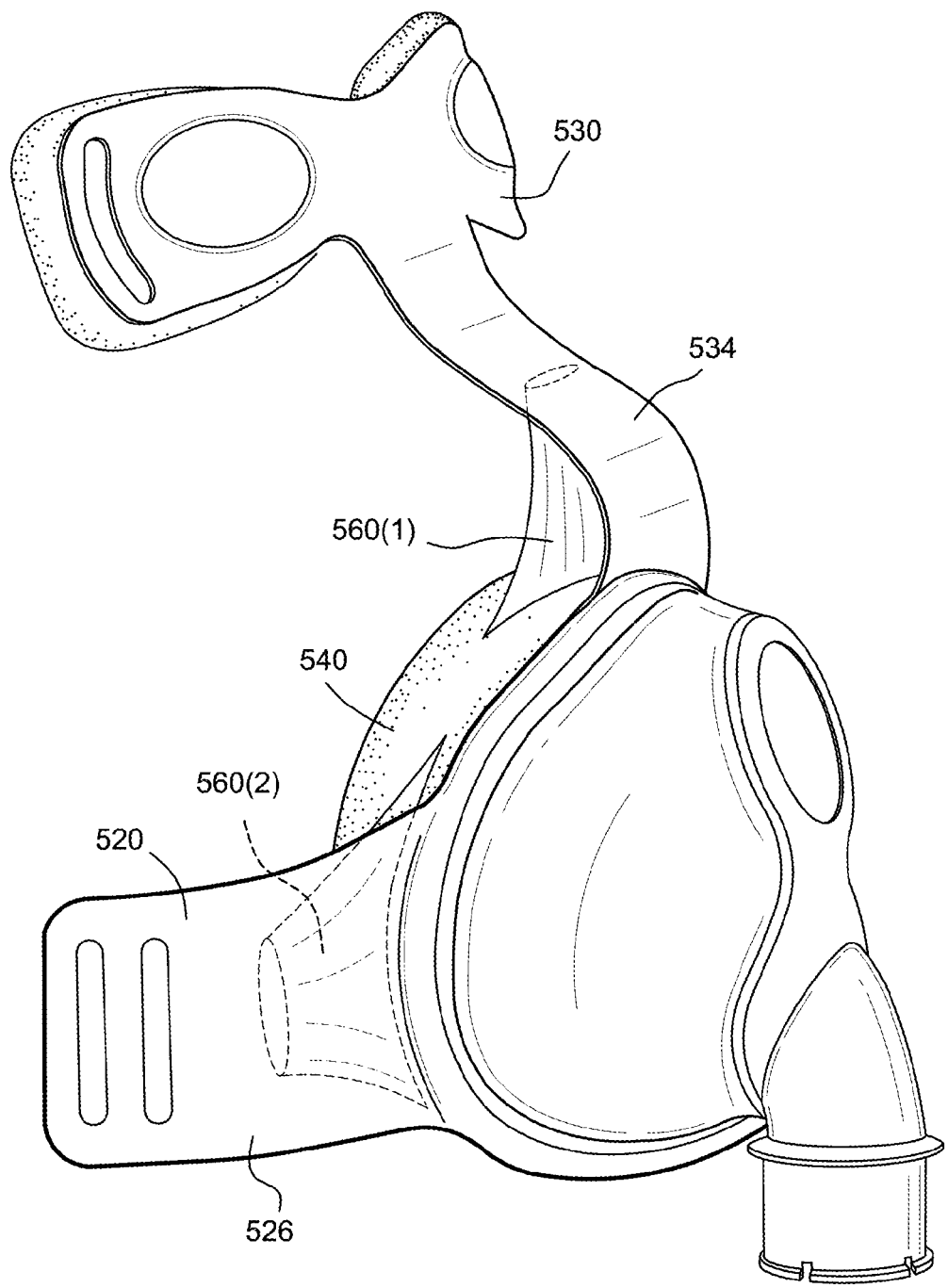
Figures 4, 5, 6, 7, 8, 9, 10, 11, 12:
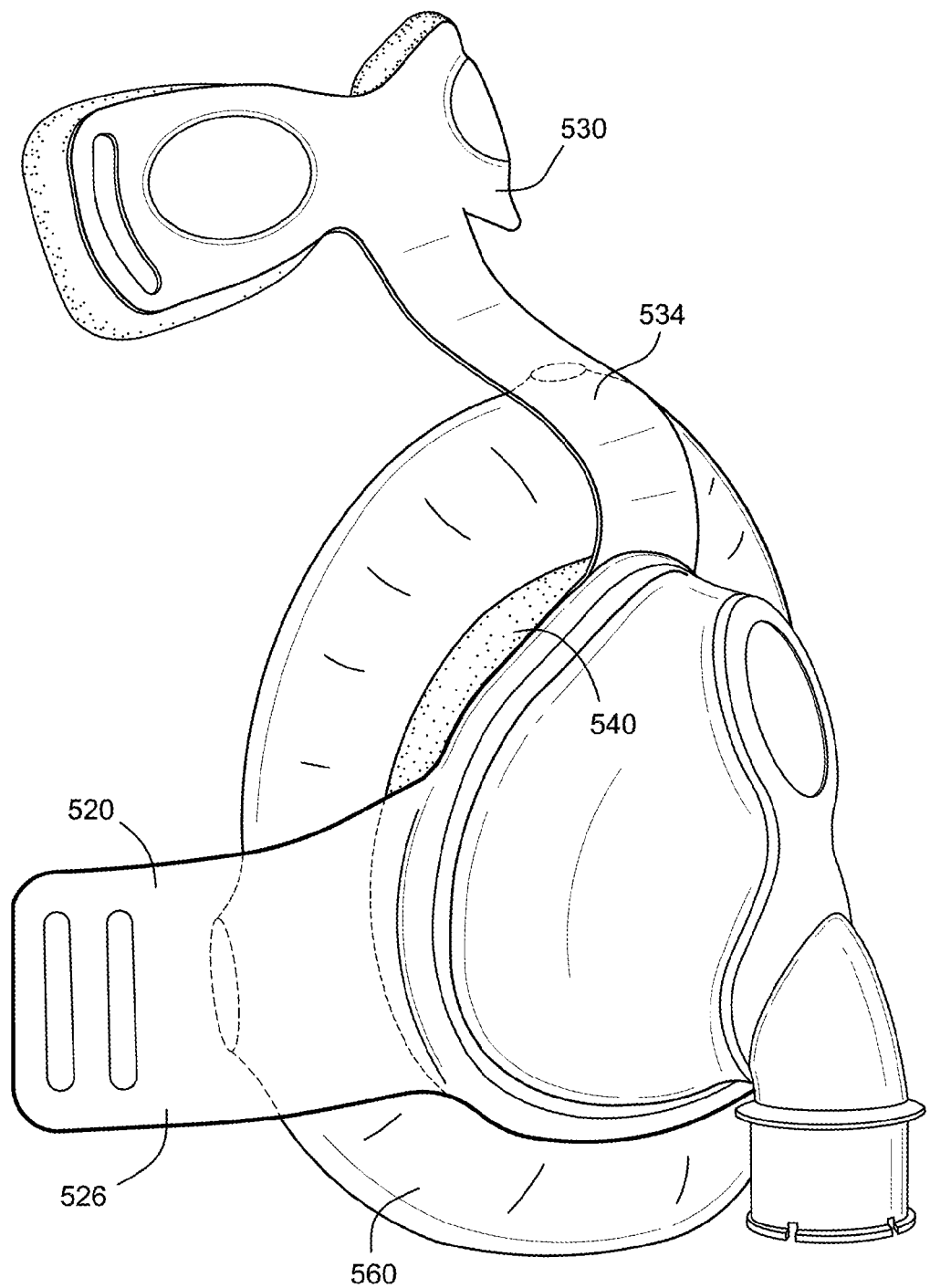
Figures 4, 5, 6, 7, 8, 9, 10, 11, 12, 13:
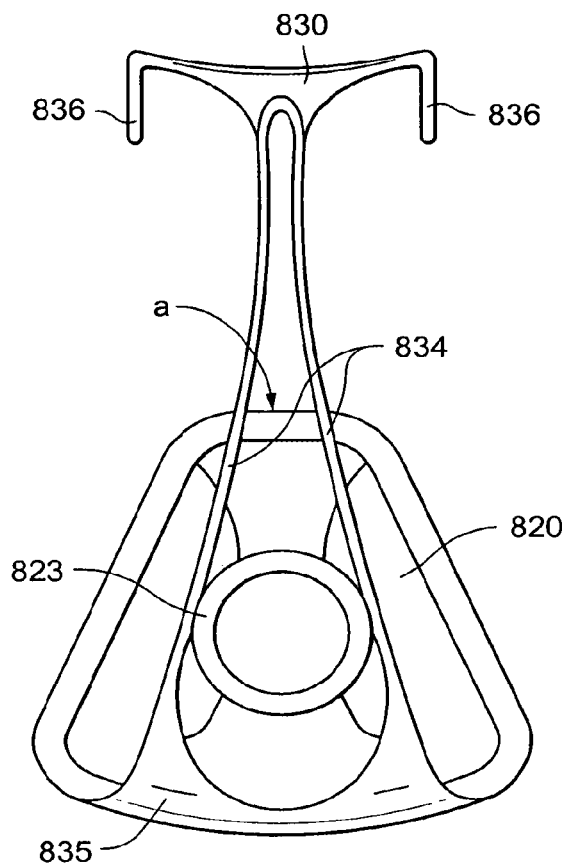
Figures 4, 5, 6, 7, 8, 9, 10, 11, 12, 13, 14:
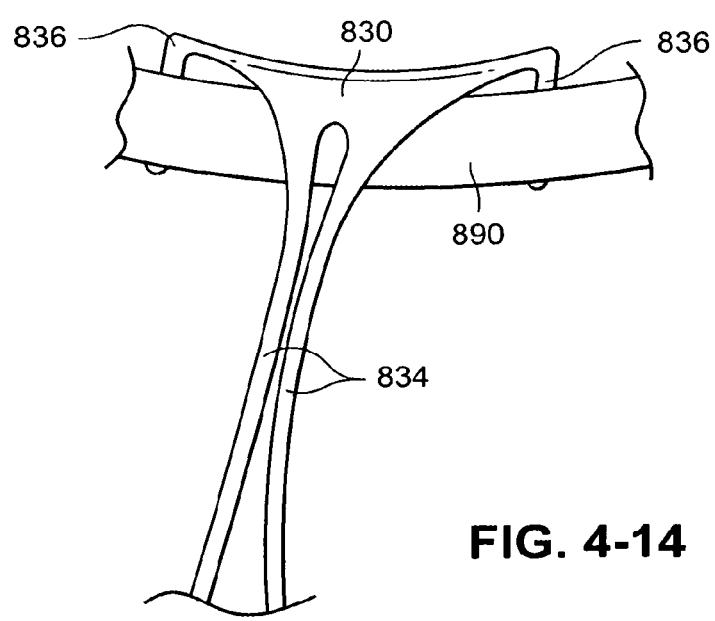
Figures 4, 5, 6, 7, 8, 9, 10, 11, 12, 13, 14, 15:
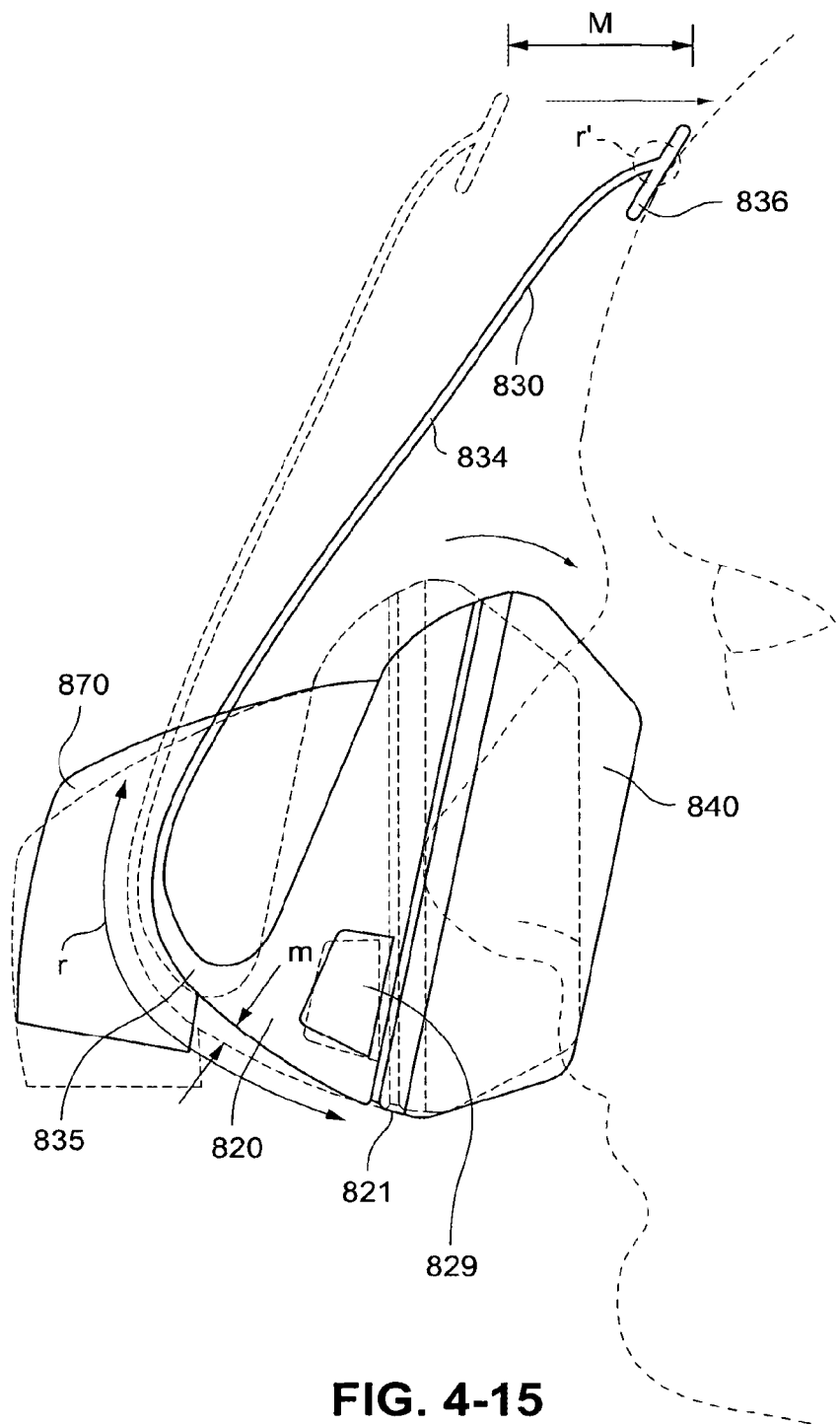
Figures 4, 5, 6, 7, 8, 9, 10, 11, 12, 13, 14, 15, 16:
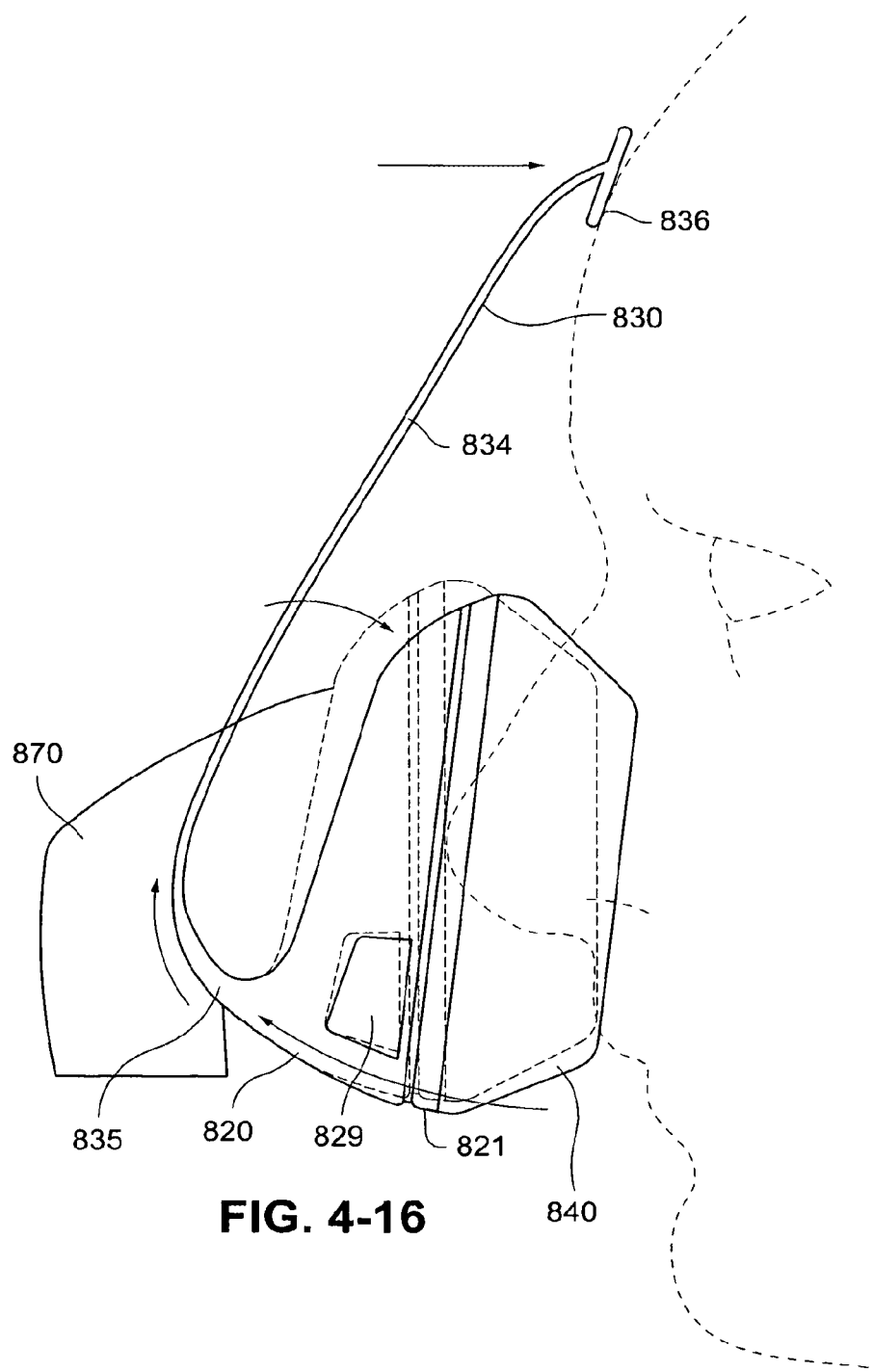
Figures 4, 5, 6, 7, 8, 9, 10, 11, 12, 13, 14, 15, 16, 17:
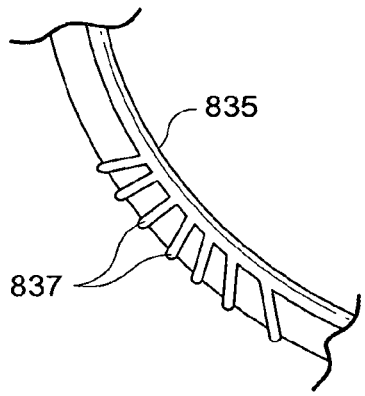
Figures 4, 5, 6, 7, 8, 9, 10, 11, 12, 13, 14, 15, 16, 17, 18:
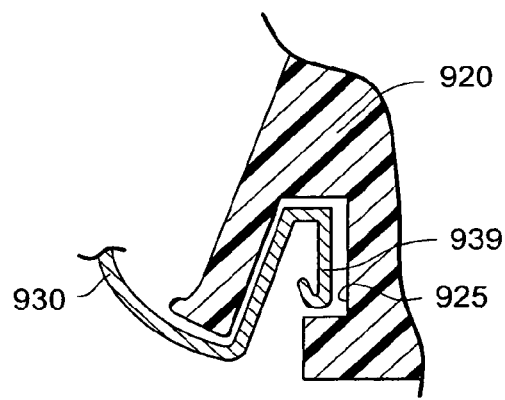
Figures 1, 5:
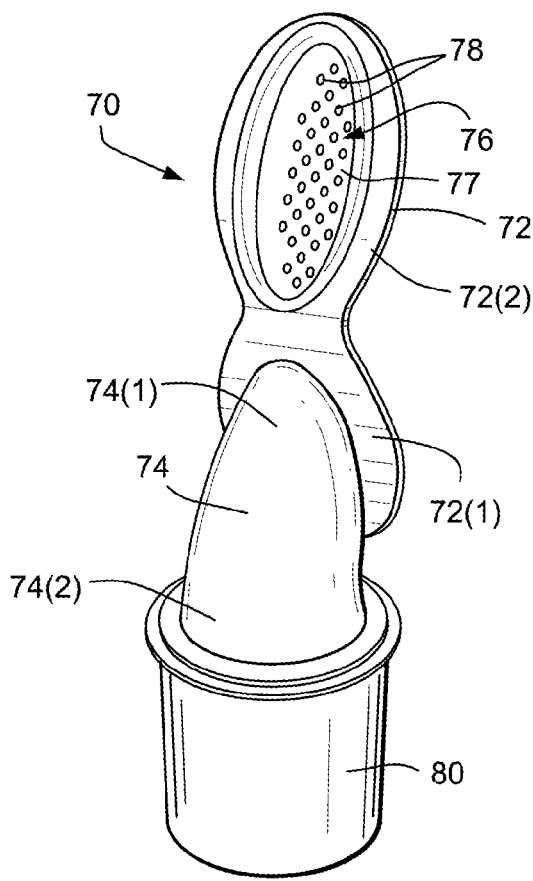
Figures 2, 5:
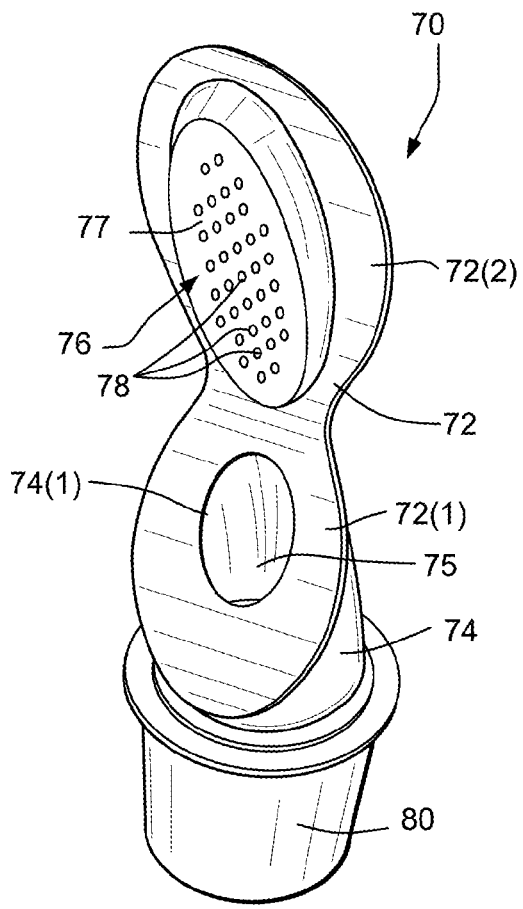
Figures 3, 5:
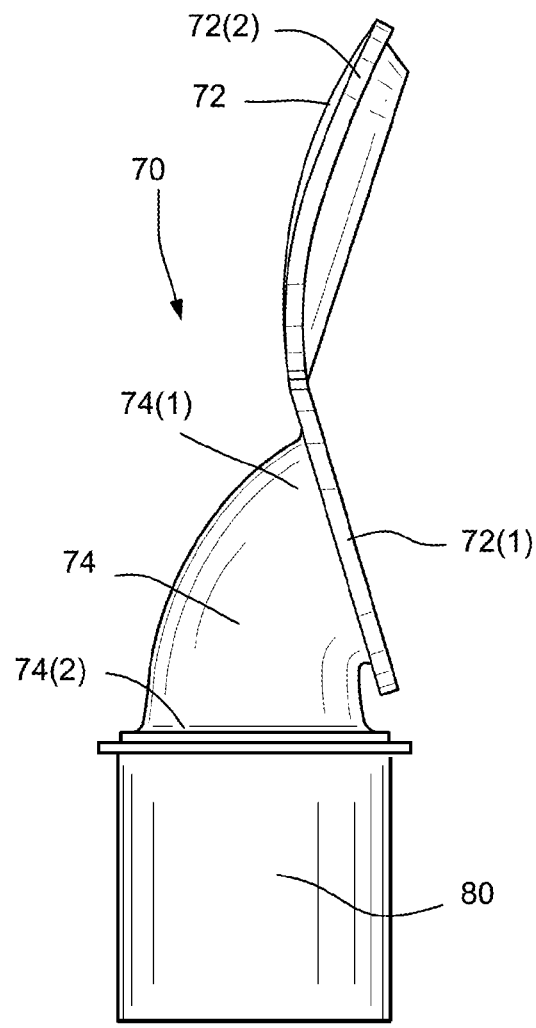
Figure 6:
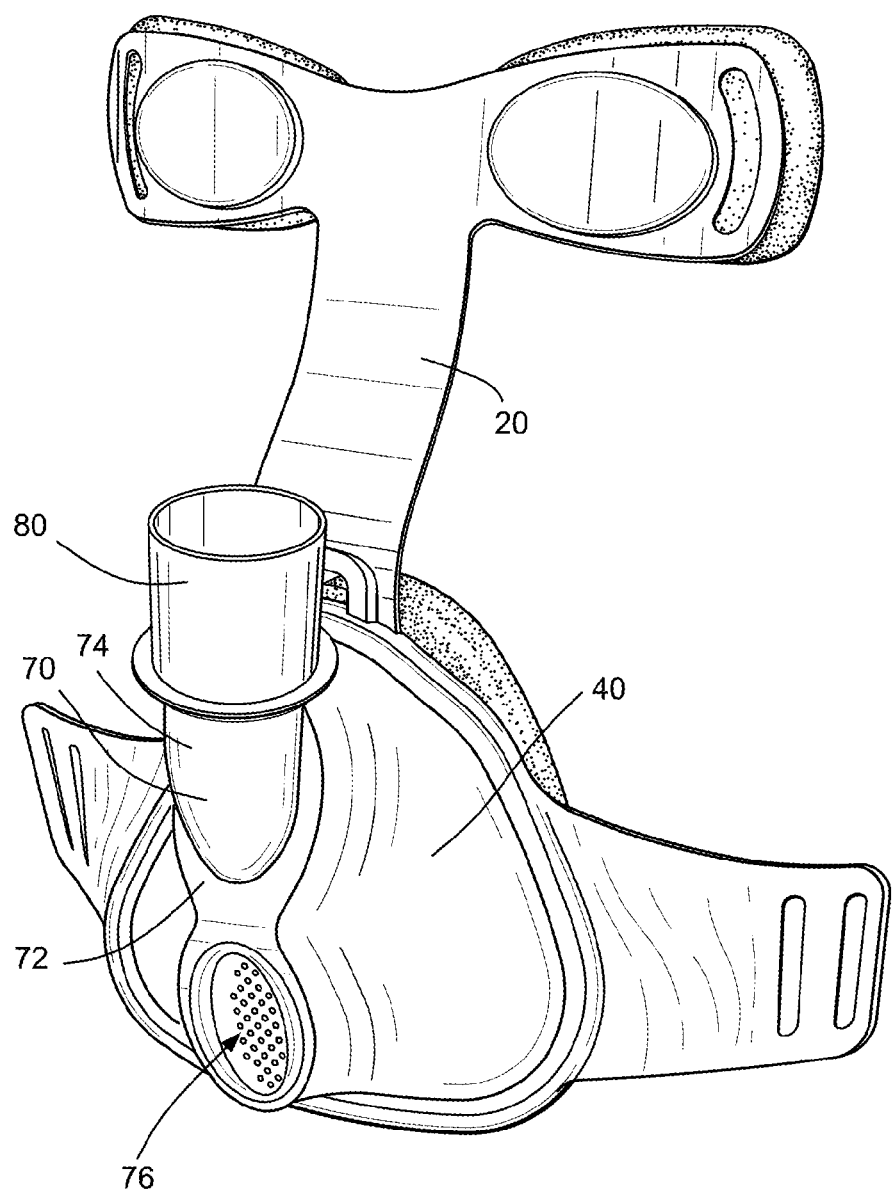
Figure 7:
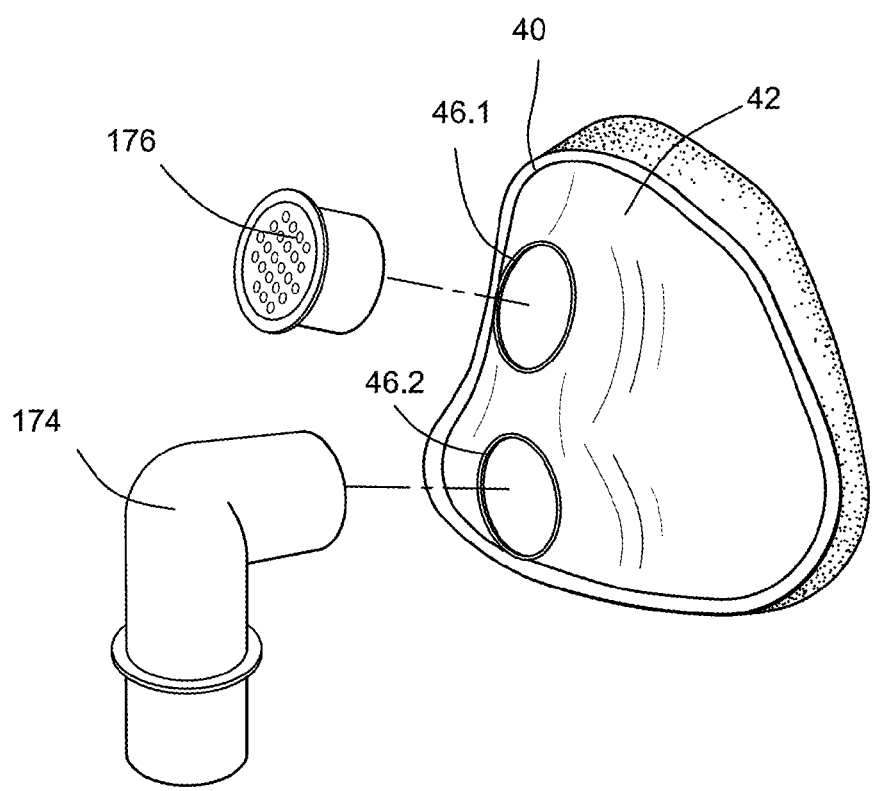
Figures 1, 8:
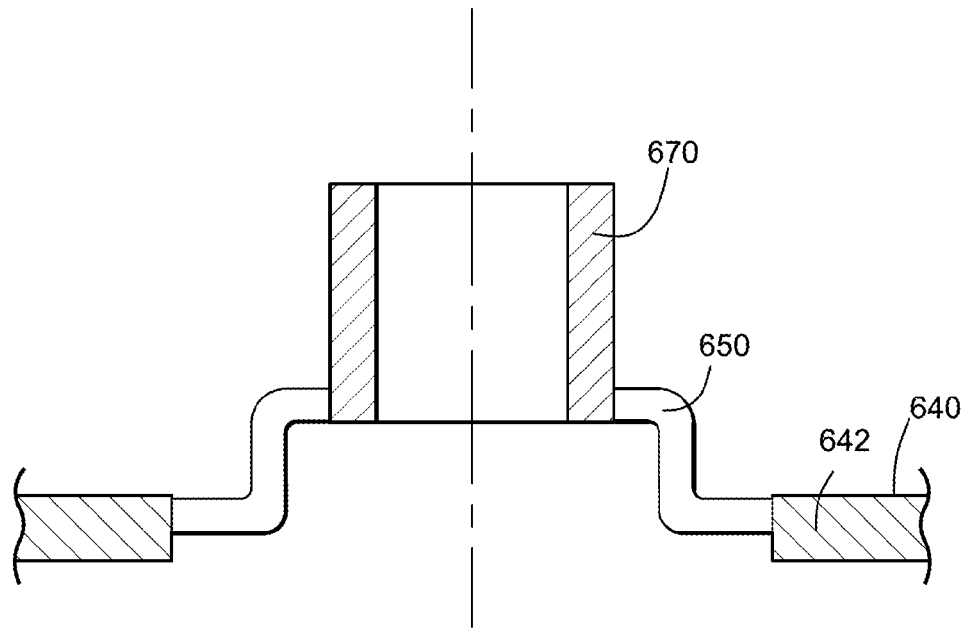
Figures 2, 8:
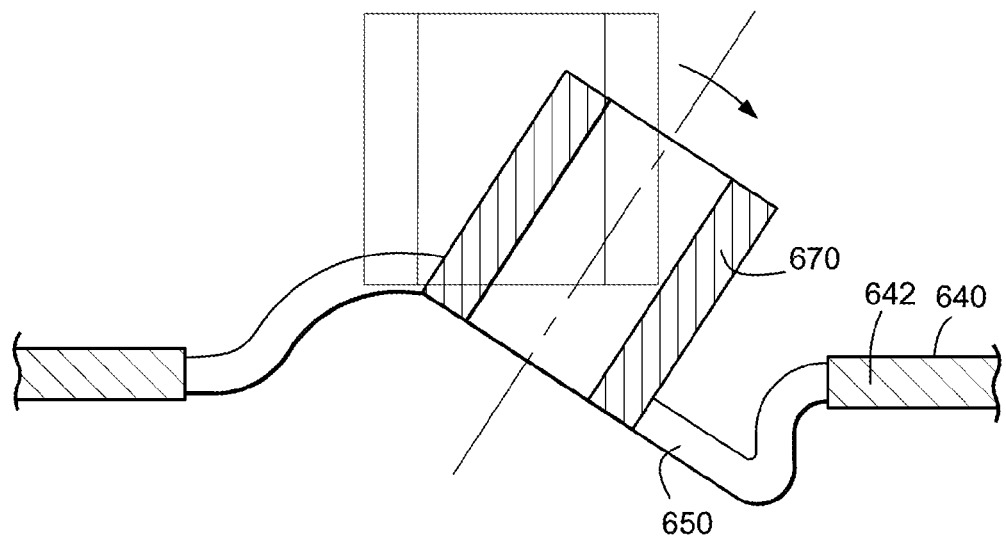
Figure 9:
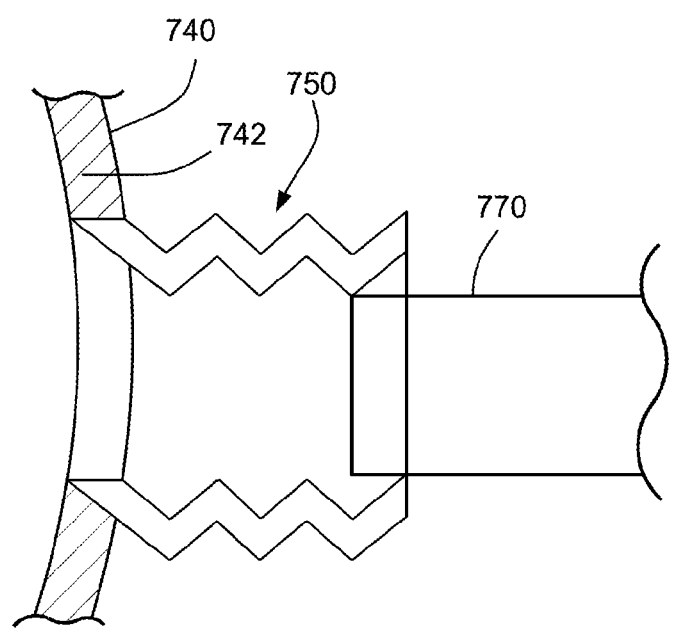

The one or more flexible members define a dynamically adjustable connector to decouple rigid connections (e.g., cushion to frame) and allow substantially free, self-fitting adjustment. It should be appreciated that such a dynamically adjustable connector may be provided between other suitable components of the mask system (e.g., between frame and elbow, between frame and headgear connectors, etc.). FIGS. 8-1 to 9 described below relate to a gusset arrangement between the elbow and frame/cushion module to enhance flexibility and reduce tube drag.

In the embodiment of FIG. 4-7, a lower end of the cushion module 240 is pivotally mounted to the frame module 220 (e.g., via pivot 202), and an upper end of the cushion module 240 is coupled to the base 234 of the forehead support 230 by at least one flexible member 260. As illustrated, the base 234 of the forehead support 230 includes a series of spaced apart protrusions or locking lugs 204 along its length that allows the flexible member 260 to be retained in different positions on the base 234, e.g., to adjust the biasing force provided by the flexible member 260 and/or adjust the initial position or angle of the cushion module 240 with respect to the frame module 220.

In the embodiment of FIG. 4-8, a lower end of the cushion module 340 is pivotally mounted to the frame module 320 (e.g., via pivot 302), and an upper end of the cushion module 340 is coupled to a lower end of the base 334 of the forehead support 330 by at least one flexible member 360. The cushion module 340 includes a lip 341 to support one end of the flexible member 360 while the opposite end of the flexible member 360 is supported by the lower end of the base 334. In the illustrated embodiment, the flexible member 360 is oriented substantially perpendicular to the patient's face in use.

In the embodiment of FIGS. 4-9 and 4-10, an upper end of the cushion module 440 is coupled to the base 434 of the forehead support by a flexible member 460(1), and opposing sides of the cushion module 440 are coupled to respective arms 426 of the frame module 420 by flexible members 460(2), 460(3). In the illustrated embodiment, each flexible member 460(1), 460(2), 460(3) includes a flexible arm portion 462 and a head portion 464 provided to the free end of the arm portion 462. The base 434 and arms 426 each include a tapered opening for removably securing a respective head portion 464 of the flexible members 460(1), 460(2), 460(3) in position.

In the embodiment of FIG. 4-11, an upper end of the cushion module 540 is coupled to the base 534 of the forehead support 530 by a flexible member 560(1), and opposing sides of the cushion module 540 are coupled to respective arms 526 of the frame module 520 by respective flexible members (only the flexible member 560(2) being visible in FIG. 4-11). In the illustrated embodiment, each flexible member has a web-like configuration that tapers from the cushion module to its attachment to the forehead support/frame.

FIG. 4-12 illustrates an alternative version of FIG. 4-11. In this embodiment (indicated with similar reference numerals to FIG. 4-11), the three web-like flexible members are replaced by a single, continuous flexible member or "trampoline-like" membrane 560. As illustrated, the single, continuous flexible member 560 is a continuous piece or web that extends around the perimeter of the cushion module 540 to connect the cushion module to the frame module 520. The single, continuous flexible member 560 may be connected to the frame module 520 in one or more locations, e.g., coupled to the base 534 of the forehead support 530 and respective arms 526 of the frame module 520. The single, piece web or flexible member may act like a gusset (e.g., similar to ResMed's Activa mask), but it is secured at one or more points on the frame, so it has the benefits of a gusset while also providing the benefits of a dynamic adjustable connector.

In each embodiment, the cushion module may be adjusted or flexed from a minimum position (i.e., the position of the cushion module when no force is applied to the cushion module by the patient) to a maximum position (i.e., the position of the cushion module when the patient applies force to the cushion module until the cushion module can move no further with respect to the frame module). The maximum position may be imposed by the frame module (e.g., the cushion module engages the frame module so it cannot extend past the frame module) or by the one or more flexible members (e.g., the spring force of the one or more flexible members will not allow further adjustment of the cushion module).

There are an infinite number of cushion module positions between the minimum and maximum positions because the flexible member is elastic. Additionally, there are no locking mechanisms in place to restrict or limit the movement of the cushion module between the minimum and maximum positions.

The one or more flexible members ensure that the angle of the cushion module is optimal for sealing engagement with a patient's face as it will flex to align the cushion module to match the shape or angle of the patient's face. The one or more flexible members may be positioned such that forces applied to the cushion module by the flexible member(s) will urge or bias the cushion module towards the patient's face, thereby enhancing the seal. For example, the one or more flexible members may be positioned such that the distance between the cushion module and the frame module is at a maximum position and the one or more flexible members are stretched. Thus, when the cushion module is applied to the face, the spring force of the elastic flexible member(s) will urge the cushion module against the face of the user.

The one or more flexible members may be connected from any position on the cushion module to any position on the frame module/forehead support. For example, the flexible member(s) may be connected from the top of the cushion module to the base of the forehead support (see FIGS. 4-7 and 4-8) and/or the flexible member(s) may be connected from the side of the cushion module to the frame module (see FIGS. 4-9 to 4-11).

The one or more flexible members may be permanently attached to the cushion module and/or frame module/forehead support by any suitable means, e.g., gluing, welding, co-molding. Alternatively, the one or more flexible members may be temporarily or releasably attached to the cushion module and/or frame module/forehead support by any suitable means, e.g., mechanical connection, interference fit, snap fit, hook and loop.

The length of each flexible member may be adjustable so that the patient can vary the elasticity of the flexible member. This may be advantageous in increasing or decreasing the spring force applied to the cushion module, resulting in varied forces on the patient's face. For example, the patient may wish to increase the force of the cushion module on their face so may increase the tension in the one or more flexible members to increase the elastic or spring force on the cushion module.

The width of each flexible member may be about 1-100 mm. In an embodiment, each flexible member may be no wider than the frame module so as to avoid interfering with the patient's line of sight and also to reduce the obtrusiveness of the mask system. In another embodiment, the width of each flexible member may not be uniform, e.g., width of the flexible member varies along its length (e.g., hourglass shaped). This arrangement may be provided to vary the elastic properties of the flexible member.

Each flexible member may be composed of any material or combination of materials that allow the desired level of flexibility, elasticity, or spring constant. For example, each flexible member may be one piece made from silicone, may include a combination of materials, or may include the same material with different properties.

In the illustrated embodiment, one or more flexible members may join the cushion module to the frame module (e.g., one flexible member in FIGS. 4-7 and 4-8 and three flexible members in FIGS. 4-9 to 4-11). Additional flexible members increase the fit range of the mask system as it is better able to adjust to the patient's face in use.

FIGS. 4-13 to 4-18 illustrate a self-fitting or auto-adjusting mask system according to another embodiment of the present invention. While the illustrated embodiment is in the form of a nasal mask, it should be appreciated that aspects of the invention may be adapted for use with other suitable interface types, e.g., full-face mask.

As illustrated, the mask system includes a frame 820 (e.g., constructed of rigid or semi-rigid material such as polycarbonate, polypropylene, etc.) and a forehead support 830 provided to the frame 820. The frame 820 provides a frame interface 821 adapted to support a flexible cushion 840 that forms a seal with the patient's face in use. The frame interface 821 may be relatively flat or planar, which may facilitate attachment (e.g., permanent (e.g., frame and cushion co-molded) or removable connection) to cushions of different configurations and/or materials (e.g., gel cushion, foam cushion, silicone cushion (e.g., silicone cushion with dual walls)). The frame 820 also provides an elbow interface 823 adapted to support an elbow 870.

The forehead support 830 is coupled to the base of the frame 820 by a movement region 835 which allows the frame 820 to flex, bend and/or pivot relative to the forehead support 830. Such movement allows adjustment of the frame 820 relative to the forehead support 830 to enhance comfort and seal of the mask system. Region 835 extends from the base of the frame and upwards towards the forehead support 830.

In the illustrated embodiment, the forehead support 830 is generally t-shaped. The base of the t-shaped forehead support may include spaced apart support members 834 that extend from the movement region 835. As shown in FIG. 4-13, the support members 834 bifurcate about the elbow interface 823 that supports the elbow. Such forehead support provides a minimalist arrangement to provide unobtrusiveness. However, the forehead support may have other suitable configurations, e.g., I-shaped.

The upper cross portion of the t-shaped forehead support may include a pair of downwardly extending arm bars 836 (although the arm bars may potentially extend upwardly). The arm bars 836 may engage with headgear straps so as to position the forehead support 830 on the forehead of the patient and secure it in place. The arm bars 836 may also engage with headgear straps with clips, ladder locks, or any other suitable attachment mechanism.

The forehead support 830 extends from the base or bottom of the frame 820, which is adjacent the patient's mouth in use. For example, the base of the frame 820 may be positioned near the patient's upper lip in a nasal mask system, or the base of the frame 820 may be positioned near the patient's lower lip in a full-face mask system, or the movement region 835 may extend from below the apex a (e.g., see FIG. 4-13) of the frame, e.g., near or below the elbow interface 823. The top or apex of the frame is positioned near the patient's nasal bridge region in both nasal and full-face mask systems (although the apex of the frame could also be positioned lower down the patient's nose).

The movement region 835 extends generally along a length of the base of the forehead support, e.g., along region r shown in FIG. 4-15. However, it should be appreciated that the movement region may extend along the entire length of the base of the forehead support or one or more selected portions of the forehead support. Also, region r may be confined to an even smaller extent, e.g., only at the base. It should be noted that relatively small movement (m) near the base can result in a relatively large movement (M) of the forehead support (see FIG. 4-15), e.g., M may be 2-10×m or more. In an embodiment, a movement region r' may be provided adjacent the arm bars 836 to allow the arms bars to flex, bend and/or pivot relative to support members 834.

The movement region 835 is contoured along its length and includes suitable dimensions (e.g., thickness) to provide flexing, bending and/or pivoting and allow a range of adjustment. In an embodiment, the movement region may be in the form of a spring arm or may be a pivot joint with a spring to bias the forehead support 830 in the desired direction, e.g., as shown in FIG. 4-15.

The location of the movement region 835 along a lower region of the frame, e.g., within the region r shown in FIG. 4-15, allows the forehead support to force the frame into the patient's face as described below.

In the illustrated embodiment of FIG. 4-15, the forehead support 830 is molded in one piece (e.g., co-molded) with the base of the frame 820 (i.e., at the movement region 835) to facilitate flexibility and movement in this area. The forehead support 830 may be made from a polymer such as polycarbonate, polypropylene, nylon, TPE, etc.

An upper strap 890 of the headgear can be positioned around the head of the patient and through the upper cross portion of the forehead support 830, e.g., under the base 834 and over respective arm bars 836 as shown in FIG. 4-14. One or more portions of the forehead support (e.g., arm bars) may be over-molded (e.g., with silicone) to help retain the upper straps in position. Such arrangement reduces parts and allows the straps to nest in the forehead support as illustrated. However, the upper cross portion of the t-shaped forehead support may have other suitable configurations, e.g., arms with slots to receive respective headgear straps.

As shown in FIG. 4-17, one or more flexible ribs 837 may be provided along the movement region 835 of the forehead support. The flexible ribs 837 may be made from a more flexible material (e.g., such as Santoprene™, silicone, etc.) than the remainder of the forehead support to enable greater adjustment of the movement region. In an embodiment, the ribs may be co-molded over the movement region and/or embedded within the thickness of the movement region (e.g., one or more notches or cut-outs provided along length of movement region and then notches filled with more flexible material to modify flexibility).

In an alternative embodiment, as shown in FIG. 4-18, the forehead support may be detachably connected to the frame. As illustrated, the base of the forehead support 930 (e.g., constructed of a titanium alloy) may include a resilient clip portion 939 that is structured to resiliently deflect into a cavity 925 provided to the base of the frame 920, e.g., with a snap-fit.

The movement region 835 allows coarse adjustment (e.g., larger tuning movement) and fine adjustment (e.g., smaller or minute tuning movement) of the cushion 840 provided to the frame 820. As shown in FIG. 4-15, coarse adjustment may be achieved by adjusting the headgear straps to achieve fit. That is, the movement region preloads the forehead support such that it is positioned away from the patient's forehead in its relaxed state (see dashed lines in FIG. 4-15). The upper headgear straps can then be tightened to pull the forehead support towards the patient's forehead (see solid lines in FIG. 4-15), which tightening will translate forces down the forehead support and into the movement region, and thus force the cushion into the patient's face.

As shown in FIG. 4-16, fine adjustment may be achieved by manipulating (or automatic adjustment inherent to the amount of force deflection built into the movement region 835) the movement region 835 to apply light pressure to the cushion to achieve comfort and seal. That is, the frame and cushion may be manipulated or flexed relative to the forehead support (which remains relatively fixed in position relative to the patient) to adjust the position of the cushion for enhanced comfort and seal (as indicated by dashed and solid lines in FIG. 4-16).

In an embodiment, the location of the movement region of the forehead support along a lower region of the frame may allow the forehead support to force the frame into the patient's face without the use of lower headgear straps. However, lower headgear straps may be connected to the frame to enhance the seal of the cushion. For example, as shown in FIGS. 4-15 and 4-16, lower strap connectors 829 (e.g., headgear clip receptacles or slots) may be positioned along lower sides of the frame 820, e.g., to anchor the movement region 835 on the patient's face.

1.3 Elbow Module

As best shown in FIGS. 2 and 5-1 to 5-3, the elbow module 70 includes an interfacing structure 72 structured to interface or otherwise attach to the cushion module 40, an elbow 74 provided to one end 72(1) of the interfacing structure 72, and a vent arrangement 76 provided to the other end 72(2) of the interfacing structure 72 for gas washout. As illustrated, the elbow module 70 provides a relatively low profile with reduced bulk.

The elbow module 70 may be constructed of a relatively rigid material similar to the main body 42 of the cushion module 40 (e.g., polycarbonate) or the elbow module 70 may be constructed of a softer material (e.g., TPE or silicone). In an embodiment, the elbow module 70 may be constructed of a material in the range of about 60-100 durometer, e.g., 80 durometer.

In an embodiment, the vent arrangement 76 and elbow 74 may be constructed of different materials, e.g., specific to vent and elbow functions. Also, the elbow module 70 may include overmolding, texturing, and/or flocking, e.g., similar to the frame module 20 described above.

The elbow module 70 pairs vent flow with impedance. This allows vent flow and/or impedance to be optimally designed or changed by altering the elbow module. That is, one piece may be changed to change the vent arrangement and/or the elbow size, e.g., if requirements change for the PAP (positive airway pressure) device. In addition, the vent arrangement 76 is fixed and positioned away from the elbow outlet 75 so that the outlet will not impede vent flow and vice versa, e.g., to provide optimal gas washout.

In the illustrated embodiment, the ends 72(1), 72(2) of the interfacing structure 72 are sloped or angled with respect to one another as best shown in FIG. 5-3. This arrangement may help to orient the direction of the vent arrangement and/or elbow.

In an embodiment, the mask system may be provided with a number of different elbow modules 70, e.g., each having a vent arrangement and/or elbow of different styles and/or sizes. For example, each elbow module may include structure as required for different operating pressures. This provides a modular arrangement that allows the cushion module 40 to be selectively and removably coupled to one of multiple elbow modules 70.

1.3.1 Elbow

The elbow 74 includes a first portion 74(1) provided to the interfacing structure 72 and a second portion 74(2) provided to a swivel joint 80 adapted to be connected to an air delivery tube. In the illustrated embodiment, the second portion 74(2) includes snap-fit tabs to connect the second portion 74(2) to the swivel joint 80. As illustrated, the elbow may taper from a larger internal diameter at the second portion 74(2) to a smaller internal diameter at the first portion 74(1).

1.3.2 Vent Arrangement

The vent arrangement 76 is positioned on a relatively flat portion 77 of the interfacing structure 72. Moreover, the relatively flat portion 77 is recessed with respect to the peripheral edge of the interfacing structure 72. As illustrated, the relatively flat portion 77 has a generally oval shape. However, the interfacing structure 72 may include other suitable structure to support the vent arrangement 76, e.g., contoured surface, concave surface, etc.

In the illustrated embodiment, the vent arrangement 76 includes a plurality of holes 78 arranged in a five column pattern. The five column pattern includes a center column, flanked by intermediate columns, which in turn are flanked by outside columns. As illustrated, the columns are substantially aligned or parallel to a longitudinal axis of the elbow.

The center column includes 3-20 holes, e.g., 9 holes, the intermediate columns each include 3-20 holes, e.g., 8 holes, and the outside columns each include 3-20 holes, e.g., 5 holes. As illustrated, the holes in the center column are offset with the holes in the intermediate columns. Also, holes in the center column are aligned with the holes in the outside columns, with the center column having two additional holes at the upper and lower ends.

In the illustrated embodiment, each hole may have a generally part conic shape, including opposed walls that converge from a larger (inside) diameter to a smaller (outside) diameter, as viewed in the direction of exhausted gas. However, other hole configurations are possible, e.g., larger (outside) diameter and smaller (inside) diameter.

However, it should be appreciated that the vent arrangement 76 may include other suitable hole arrangements, hole numbers, and/or hole shapes.

1.3.3 Elbow Module Attachment to Cushion Module

The main body 42 of the cushion module 40 is structured to maintain the elbow module 70 in an operative position with respect to the patient's face.

In the illustrated embodiment, the opening 46 of the main body 42 includes a flange or interfacing structure 47 along its peripheral edge that is adapted to interface with or otherwise removably connect to the interfacing structure 72 of the elbow module 70. The interfacing structures 47, 72 may connect with a friction fit, snap-fit, mechanical interlock, or other suitable attachment mechanism. However, other suitable arrangements for attaching the elbow module 70 to the cushion module 40 are possible.

The opening 46 of the cushion module 40 and the interfacing structure 72 of the elbow module 70 include complementary shapes. In the illustrated embodiment, the opening 46 and interfacing structure 72 each include a figure-8 or hourglass-type shape. Such shape allows the elbow module 70 to be attached to the cushion module 40 in one of only two orientations. This allows the patient to select between two routings of the air delivery tube.

1.3.4 Alternative Tube Routings

The elbow module 70 may be attached to the cushion module 40 in a first orientation (as shown in FIGS. 1-1 to 1-3) so that the elbow extends downwardly from the mask to direct the air delivery tube under the patient's head in use. Alternatively, the elbow module 70 may be rotated and attached to the cushion module 40 in a second orientation (as shown in FIG. 6) so that the elbow extends upwardly from the mask to direct the air delivery tube over the patient's head in use.

The different orientations of the elbow module 70 may also change the direction of vent flow from the vent arrangement 76. For example, in the second orientation of the elbow module 70 (FIG. 6), the vent arrangement 76 may direct vent flow generally towards the patient, which may be less obtrusive to the patient's bed partner. Also, the different orientations of the elbow module 70 allows different wash-out configurations without using a baffle.

1.3.5 Elbow Module Seal

In an embodiment, a seal may be provided at the interface between the elbow module 70 and the cushion module 40, e.g., around the opening 46 of the cushion module 40. For example, a seal (e.g., elastomeric, ring-shaped seal) may be formed separately from the elbow module 70 and the cushion module 40 and attached at the interface between the elbow module 70 and the cushion module 40 (e.g., sandwiched between elbow module/cushion module connection, adhesive, etc.). Alternatively, a seal may be co-molded with one of the elbow module 70 and cushion module 40. For example, the elbow module 70 may be molded of a material (e.g., polycarbonate) and the seal may be co-molded onto the elbow module 70 of a relatively soft elastomeric material (e.g., TPE, silicone). In another embodiment, the elbow module 70 and/or cushion module 40 may include overlapping material to provide a seal, e.g., elbow module includes overlapping material that overlaps frame module at the interface to provide a seal.

1.3.6 Alternative Elbow/Vent Arrangement

In an alternative embodiment, the elbow module may be replaced with separate vent and elbow modules. In such arrangement, as shown in FIG. 7, the main body 42 of the cushion module 40 may include a pair of openings 46.1, 46.2, one to receive a vent module 176 and one to receive an elbow module 174. The vent module 176 and elbow module 174 may be structured to rotate or swivel with respect to the main body 42. Also, the vent module 176 and/or elbow module 174 may be constructed of relatively soft or hard material, and may include a seal at the interface with the main body 42.

In another embodiment, the elbow module may be flexibly attached to the cushion module to allow the elbow module to move freely thereby reducing tube drag affects.

For example, as shown in FIGS. 8-1 and 8-2, a flexible gusset 650 may be provided between the elbow module 670 and the main body 642 of the cushion module 640. As illustrated, the gusset 650 is constructed of a flexible material (e.g., elastomeric) and is contoured or bent along its length (i.e., gusset 650 extends upwardly from its connection to the main body 642) in order to allow a range of axial and lateral movement. That is, the gusset 650 adds flexibility and articulation of the elbow module in use, e.g., to reduce tube drag.

Thus, when the tube forces the elbow module to move, the gusset will absorb the force thereby decreasing the risk of altering the position of the cushion module with respect to the patient's face and potentially disrupting the seal. FIG. 8-1 illustrates an initial position of the elbow module 670 (i.e., the position when no force is applied to the elbow module, e.g., by the tube), and FIG. 8-2 illustrates a deflected position of the elbow module 670 (i.e., the position when force is applied to the elbow module, e.g., by the tube). As illustrated, the gusset 650 bends or deforms without affecting the cushion module 640.

In yet another embodiment, a series of gussets may be provided between the elbow module and the cushion module. For example, as shown in FIG. 9, a concertina or bellows arrangement 750 may be provided between the elbow module 770 and the main body 742 of the cushion module 740, e.g., to absorb tube drag forces. As illustrated, the concertina arrangement includes a series of folds that allows a range of axial and lateral movement.

It should be appreciated that such flexible gusset may be used to attach an elbow to a mask frame.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system for delivery of a flow of breathable gas at a continuously positive pressure to an entrance of a patient's airways, wherein the mask system is configured to maintain a therapy pressure in a range of about 2-30 cm $H_2O$ while the patient is sleeping to ameliorate sleep disordered breathing, the mask system comprising:

a cushion module including a main body and a nasal cushion connected to the main body,
wherein the main body includes an inlet opening structured to receive the flow of breathable gas at the therapy pressure for breathing by the patient,
wherein the nasal cushion is constructed and arranged to form a seal with a patient's nose,
wherein the main body and the nasal cushion form a breathing chamber pressurizable to the therapy pressure, and
wherein the main body is more rigid than the nasal cushion;
a frame movably coupled to the cushion module,
wherein the frame includes a retaining portion and a forehead support that extends from a top of the retaining portion,
wherein the retaining portion is structured and arranged to retain the frame to the main body of the cushion module, and
wherein the forehead support includes an elongated neck and a pair of upper headgear connectors;
headgear to maintain the mask system in position on a head of the patient, the headgear including a pair of upper straps, each of the pair of upper straps adapted to connect to a respective one of the pair of upper headgear connectors of the forehead support; and
a flexible elastic member arranged between the frame and the cushion module,
wherein the flexible elastic member includes a first end and a second end opposite to the first end,
wherein the first end is coupled to the elongated neck of the forehead support and the second end is coupled to the main body of the cushion module, wherein the flexible elastic member is arranged outside the breathing chamber, wherein the frame is movable relative to the cushion module from an initial position to an adjusted position, wherein the flexible elastic member is arranged to provide a biasing force between the frame and the cushion module to bias the frame to the initial position, wherein the frame is movable from the initial position against biasing from the flexible elastic member to the adjusted position to adjust an angle of the frame with respect to the cushion module, and wherein the flexible elastic member is configured to allow automatic self-adjustment of the frame with respect to the cushion module.

2. The mask system according to claim 1, further comprising an elbow structured to connect to an air delivery tube to deliver the flow of air at the therapy pressure to the breathing chamber of the cushion module, wherein the elbow is configured to communicate with the cushion module through the inlet opening of the main body.

3. The mask system according to claim 2, wherein the elbow includes a vent arrangement including a plurality of holes for gas washout.

4. The mask system according to claim 1, wherein the flexible elastic member comprises silicone.

5. The mask system according to claim 1, wherein the second end of the flexible elastic member is coupled to the main body superior to the inlet opening.

6. The mask system according to claim 1, wherein the first end of the flexible elastic member is coupled to a lower end of the elongated neck, and wherein the pair of upper headgear connectors are provided to an upper end of the elongated neck that is opposite to the lower end.

7. The mask system according to claim 1, further comprising a pair of lower headgear connectors, each of said pair of lower headgear connectors comprising a clip arrangement configured to connect to the main body of the cushion module.

8. The mask system according to claim 1, wherein the nasal cushion includes a base wall attached to the main body and a membrane adapted to form said seal.

9. The mask system according to claim 1, further comprising a pivotal coupling to pivotally couple the frame to the main body of the cushion module, wherein the flexible elastic member is arranged superior to the pivotal coupling.

10. The mask system according to claim 1, wherein the frame is separately attachable to the cushion module to allow removal of the frame from the cushion module.

11. The mask system according to claim 1, the flexible elastic member is configured to allow automatic self-adjustment in at least towards-and-away directions of the frame with respect to the cushion module.

12. The mask system according to claim 1, wherein the first end of the flexible elastic member is permanently attached to the elongated neck of the forehead support.

13. The mask system according to claim 1, wherein the second end of the flexible elastic member is releasably attached to the main body of the cushion module.

14. The mask system according to claim 1, wherein the flexible elastic member is attached to and extends from an exterior surface of the main body of the cushion module and externally to the breathing chamber.

15. The mask system according to claim 1, wherein the flexible elastic member includes at least a portion that is configured to be oriented substantially perpendicular to the patient's face in the initial position.

16. The mask system according to claim 1, wherein the frame is configured to engage the cushion module to impose a maximum position in which the frame can move no further with respect to the cushion module.

17. The mask system according to claim 16, wherein the flexible elastic member is configured to allow an infinite number of adjusted positions between the initial position and maximum position.

18. The mask system according to claim 1, wherein the flexible elastic member includes a width that is less than a width of the elongated neck of the forehead support.

19. A CPAP system for treatment of sleep disordered breathing, the CPAP system comprising:
the mask system according to claim 1;
a flow generator structured to supply the flow of air at the therapy pressure; and
an air delivery tube connected between the flow generator and the mask system to deliver the flow of air at the therapy pressure from the flow generator to the mask system.

* * * * *